United States Patent
Bonsignore et al.

(10) Patent No.: US 7,175,654 B2
(45) Date of Patent: Feb. 13, 2007

(54) STENT DESIGN HAVING STENT SEGMENTS WHICH UNCOUPLE UPON DEPLOYMENT

(75) Inventors: Craig Bonsignore, San Jose, CA (US); Kirk Johnson, Weston, FL (US)

(73) Assignee: Cordis Corporation, Miami Lakes, FL (US)

( * ) Notice: Subject to any disclaimer, the term of this patent is extended or adjusted under 35 U.S.C. 154(b) by 369 days.

(21) Appl. No.: 10/687,143

(22) Filed: Oct. 16, 2003

(65) Prior Publication Data

US 2005/0085896 A1   Apr. 21, 2005

(51) Int. Cl.
A61F 2/06  (2006.01)
(52) U.S. Cl. ................................ 623/1.15; 623/1.11
(58) Field of Classification Search ............. 623/1.11, 623/1.15, 1.34; 606/198
See application file for complete search history.

(56) References Cited

U.S. PATENT DOCUMENTS

| | | | |
|---|---|---|---|
| 3,585,707 A | 6/1971 | Stevens | |
| 4,655,771 A | 4/1987 | Wallsten | |
| 4,733,665 A | 3/1988 | Palmaz | |
| 5,045,072 A | 9/1991 | Castillo et al. | |
| 5,254,107 A | 10/1993 | Soltesz | |
| 5,632,771 A | 5/1997 | Boatman et al. | |
| 5,725,572 A | 3/1998 | Lam et al. | |
| 5,741,327 A | 4/1998 | Frantzen | |
| 5,800,526 A | 9/1998 | Anderson et al. | |
| 5,902,332 A * | 5/1999 | Schatz | 623/1.16 |
| 6,022,374 A | 2/2000 | Imran | |
| 6,033,434 A | 3/2000 | Borghi et al. | |
| 6,143,016 A * | 11/2000 | Bleam et al. | 606/198 |
| 6,251,134 B1 * | 6/2001 | Alt et al. | 623/1.16 |
| 6,599,314 B2 * | 7/2003 | Mathis | 623/1.11 |
| 6,623,518 B2 * | 9/2003 | Thompson et al. | 623/1.11 |
| 6,709,454 B1 * | 3/2004 | Cox et al. | 623/1.16 |
| 6,863,685 B2 * | 3/2005 | Davila et al. | 623/1.34 |
| 2002/0143386 A1 | 10/2002 | Davila et al. | |
| 2003/0135266 A1 * | 7/2003 | Chew et al. | 623/1.16 |
| 2003/0139796 A1 * | 7/2003 | Sequin et al. | 623/1.12 |

FOREIGN PATENT DOCUMENTS

WO   WO 00/15151 A   3/2000
WO   WO 03/075797 A   9/2003

OTHER PUBLICATIONS

European Search Report EP 04 25 6310 dated May 3, 2005.

* cited by examiner

*Primary Examiner*—Glenn K. Dawson
*Assistant Examiner*—Kathleen Sonnett

(57) ABSTRACT

A stent or other intraluminal medical device may be constructed utilizing multiple, individual, independent, self-expanding stent segments which are designed to interlock when constrained within a delivery sheath and uncouple upon deployment. The individual segments are releasably connected by a series of bridging elements and receptacles.

7 Claims, 20 Drawing Sheets

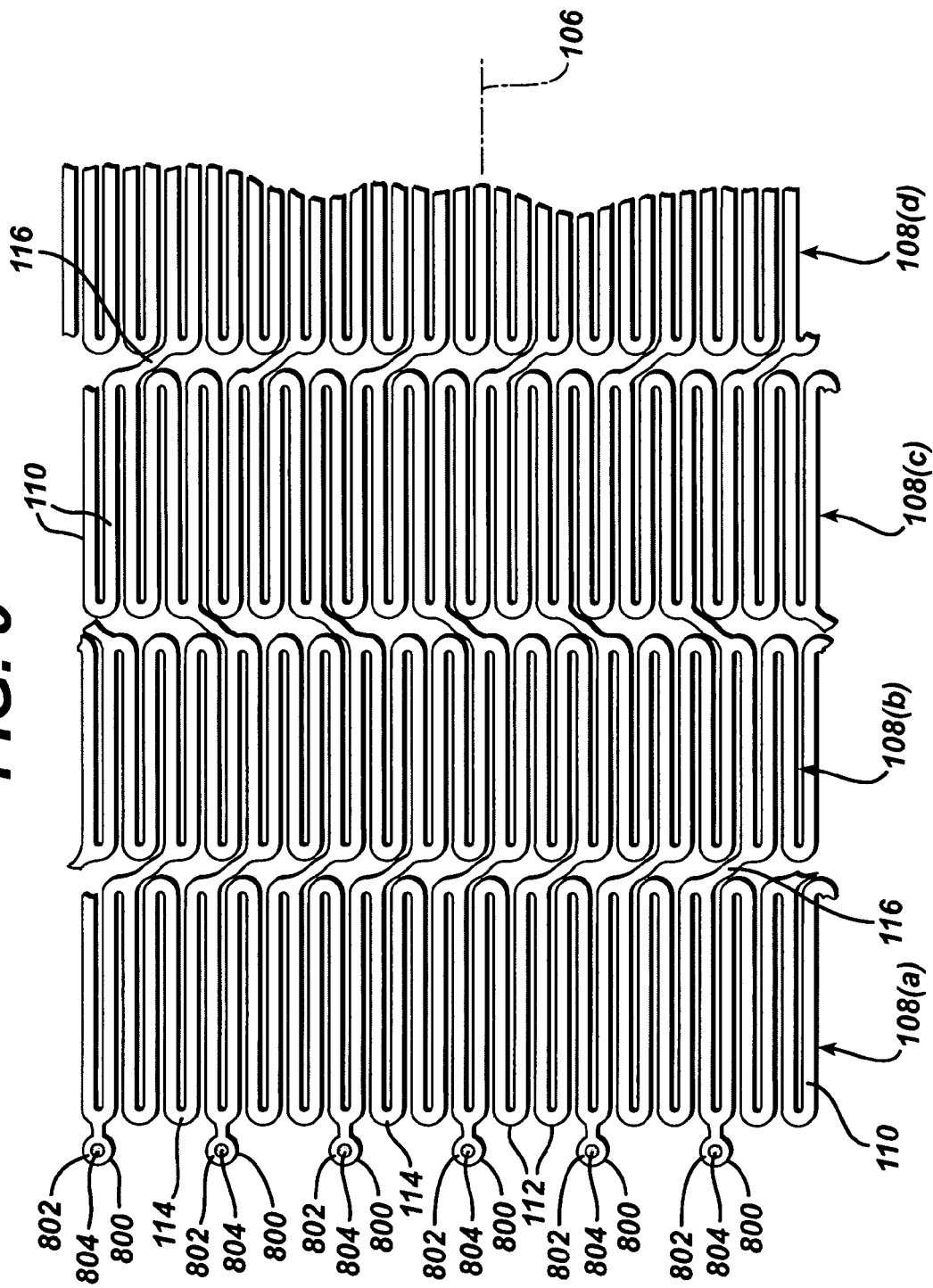

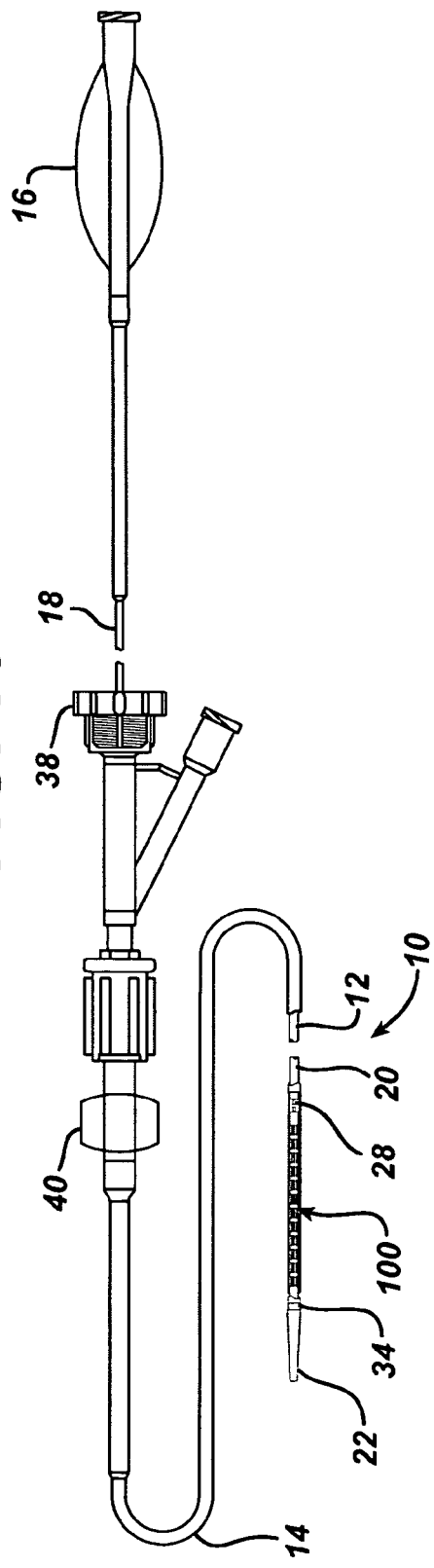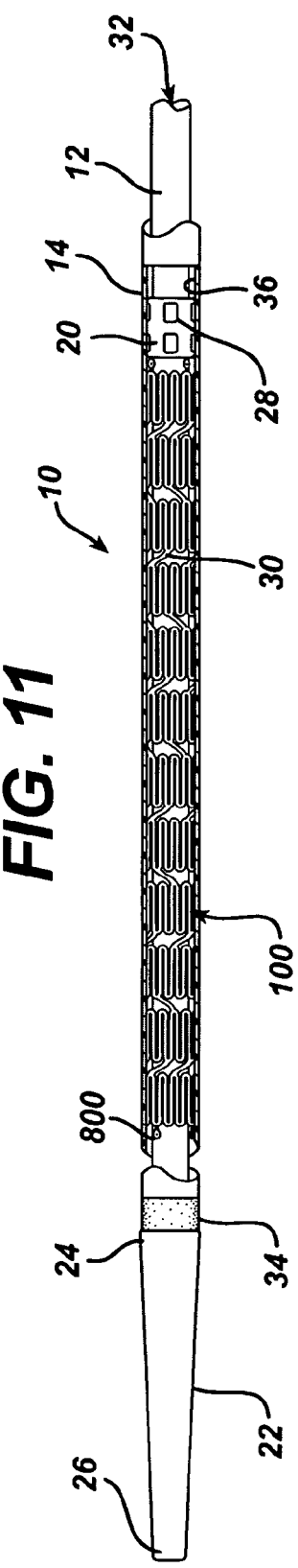

STENT DESIGN HAVING STENT SEGMENTS WHICH UNCOUPLE UPON DEPLOYMENT

BACKGROUND OF THE INVENTION

1. Field of the Invention

The present invention relates to stents having a modified bridge design and more particularly to stents having an anvil bridge design. In addition the present invention relates to intraluminal devices, and more particularly to intraluminal devices, such as stents, incorporating integral markers for increasing the radiopacity thereof. The present invention also relates to stent structures constructed from independent, interlocking stent segments which uncouple once deployed.

2. Discussion of Related Art

Percutaneous transluminal angioplasty (PTA) is a therapeutic medical procedure used to increase blood flow through an artery. In this procedure, the angioplasty balloon is inflated within the stenosed vessel, or body passageway, in order to shear and disrupt the wall components of the vessel to obtain an enlarged lumen. With respect to arterial stenosed lesions, the relatively incompressible plaque remains unaltered, while the more elastic medial and adventitial layers of the body passageway stretch around the plaque. This process produces dissection, or a splitting and tearing, of the body passageway wall layers, wherein the intima, or internal surface of the artery or body passageway, suffers fissuring. This dissection forms a "flap" of underlying tissue, which may reduce the blood flow through the lumen, or completely block the lumen. Typically, the distending intraluminal pressure within the body passageway can hold the disrupted layer, or flap, in place. If the intimal flap created by the balloon dilation procedure is not maintained in place against the expanded intima, the intimal flap can fold down into the lumen and close off the lumen, or may even become detached and enter the body passageway. When the intimal flap closes off the body passageway, immediate surgery is necessary to correct the problem.

Recently, transluminal prostheses have been widely used in the medical arts for implantation in blood vessels, biliary ducts, or other similar organs of the living body. These prostheses are commonly referred to as stents and are used to maintain, open, or dilate tubular structures. An example of a commonly used stent is given in U.S. Pat. No. 4,733,665 to Palmaz. Such stents are often referred to as balloon expandable stents. Typically the stent is made from a solid tube of stainless steel. Thereafter, a series of cuts are made in the wall of the stent. The stent has a first smaller diameter, which permits the stent to be delivered through the human vasculature by being crimped onto a balloon catheter. The stent also has a second, expanded diameter, upon application of a radially, outwardly directed force, by the balloon catheter, from the interior of the tubular shaped member.

However, one concern with such stents is that they are often impractical for use in some vessels such as the carotid artery. The carotid artery is easily accessible from the exterior of the human body, and is close to the surface of the skin. A patient having a balloon expandable stent made from stainless steel or the like, placed in their carotid artery, might be susceptible to severe injury through day-to-day activity. A sufficient force placed on the patient's neck could cause the stent to collapse, resulting in injury to the patient. In order to prevent this, self-expanding stents have been proposed for use in such vessels. Self-expanding stents act like springs and will recover to their expanded or implanted configuration after being crushed.

One type of self-expanding stent is disclosed in U.S. Pat. No. 4,655,771. The stent disclosed in U.S. Pat. No. 4,655,771 has a radially and axially flexible, elastic tubular body with a predetermined diameter that is variable under axial movement of the ends of the body relative to each other and which is composed of a plurality of individually rigid but flexible and elastic thread elements defining a radially self-expanding helix. This type of stent is known in the art as a "braided stent" and is so designated herein. Placement of such stents in a body vessel can be achieved by a device which comprises an outer catheter for holding the stent at its distal end, and an inner piston which pushes the stent forward once it is in position.

However, braided stents have many disadvantages. They typically do not have the necessary radial strength to effectively hold open a diseased vessel. In addition, the plurality of wires or fibers used to make such stents could become dangerous if separated from the body of the stent, where they could pierce through the vessel. Therefore, there has been a desire to have a self-expanding stent which is cut from a tube of metal, which is the common manufacturing method for many commercially available balloon-expandable stents. In order to manufacture a self-expanding stent cut from a tube, the alloy used would preferably exhibit superelastic or psuedoelastic characteristics at body temperature, so that it is crush recoverable.

The prior art makes reference to the use of alloys such as Nitinol (Ni—Ti alloy), which have shape memory and/or superelastic characteristics, in medical devices which are designed to be inserted into a patient's body. The shape memory characteristics allow the devices to be deformed to facilitate their insertion into a body lumen or cavity and then be heated within the body so that the device returns to its original shape. Superelastic characteristics, on the other hand, generally allow the metal to be deformed and restrained in the deformed condition to facilitate the insertion of the medical device containing the metal into a patient's body, with such deformation causing the phase transformation. Once within the body lumen, the restraint on the superelastic member can be removed, thereby reducing the stress therein so that the superelastic member can return to its original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

Shape memory characteristics are imparted to the alloy by heating the metal at a temperature above which the transformation from the martensite phase to the austenite phase is complete, i.e. a temperature above which the austenite phase is stable (the Af temperature). The shape of the metal during this heat treatment is the shape "remembered." The heat-treated metal is cooled to a temperature at which the martensite phase is stable, causing the austenite phase to transform to the martensite phase. The metal in the martensite phase is then plastically deformed, e.g. to facilitate the entry thereof into a patient's body. Subsequent heating of the deformed martensite phase to a temperature above the martensite to austenite transformation temperature causes the deformed martensite phase to transform to the austenite phase, and during this phase transformation the metal reverts back to its original shape if unrestrained. If restrained, the metal will remain martensitic until the restraint is removed.

Methods of using the shape memory characteristics of these alloys in medical devices intended to be placed within a patient's body present operational difficulties. For example, with shape memory alloys having a stable martensite temperature below body temperature, it is frequently difficult to maintain the temperature of the medical device containing such an alloy sufficiently below body temperature to prevent the transformation of the martensite phase to the austenite phase when the device was being inserted into a patient's body. With intravascular devices formed of shape memory alloys having martensite-to-austenite transformation temperatures well above body temperature, the devices can be introduced into a patient's body with little or no problem, but they must be heated to the martensite-to-austenite transformation temperature which is frequently high enough to cause tissue damage.

When stress is applied to a specimen of a metal such as Nitinol exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increases in stress are necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load, and to recover from the deformation upon the removal of the load, is commonly referred to as superelasticity or pseudoelasticity. It is this property of the material which makes it useful in manufacturing tube cut self-expanding stents.

A concern associated with self-expanding stents is that of the compressive forces associated with stent loading and stent deployment. In stent designs having periodically positioned bridges, the resulting gaps between unconnected loops may be disadvantageous, especially during loading into a stent delivery system and subsequent deployment from a stent delivery system. In both the loading and deployment situations, the stent is constrained to a small diameter and subjected to high compressive axial forces. These forces are transmitted axially through the stent by the connecting bridges and may cause undesirable buckling or compression of the adjacent hoops in the areas where the loops are not connected by bridges.

A concern with stents and with other medical devices formed from superelastic materials, is that they may exhibit reduced radiopacity under X-ray fluoroscopy. To overcome this problem, it is common practice to attach markers, made from highly radiopaque materials, to the stent, or to use radiopaque materials in plating or coating processes. Those materials typically include gold, platinum, or tantalum. The prior art makes reference to these markers or processes in U.S. Pat. No. 5,632,771 to Boatman et al., U.S. Pat. No. 6,022,374 to Imran, U.S. Pat. No. 5,741,327 to Frantzen, U.S. Pat. No. 5,725,572 to Lam et al., and U.S. Pat. No. 5,800,526 to Anderson et al. However, due to the size of the markers and the relative position of the materials forming the markers in the galvanic series versus the position of the base metal of the stent in the galvanic series, there is a certain challenge to overcome; namely, that of galvanic corrosion. Also, the size of the markers increases the overall profile of the stent. In addition, typical markers are not integral to the stent and thus may interfere with the overall performance of the stent as well as become dislodged from the stent. Also, typical markers are used to indicate relative position within the lumen and not whether the device is in the deployed or undepolyed position.

A concern with stents in general is the transmission of forces between interconnected elements. Conventional vascular stents comprise a series of ring-like radially expandable structural members that are axially connected by bridging elements. When a stent is subjected to in vivo bending, stretching or compression, its ring-like structural members distribute themselves accordingly, thus allowing the structure to conform to its vascular surroundings. These loading conditions cause the ring-like structural members to change their relative axial positions. The bridging elements constrain the ring-like structural members and therefore communicate strain between the ring-like structural members.

The structural properties of any device, including a stent, are a function of its material and construction. Many of the performance characteristics of such devices are a function of its structural properties. Important performance characteristics include the ability to reliably and repeatably manufacture and assemble the device, accurately deliver it to the intended site, the strength and flexibility of the device, and its acute and long term integrity, among many others. Accordingly, such performance characteristics are strongly influenced by the material and construction of the device. This invention describes several aspects relating to material selection and properties, including but is primarily concerned with construction. Specifically, this invention relates to geometrical configurations of stents, systems of stents, and devices for delivering such stents.

SUMMARY OF THE INVENTION

The present invention overcomes the disadvantages associated with undesirable loading effects during stent loading and stent deployment as briefly discussed above. The present invention also overcomes many of the disadvantages associated with reduced radiopacity exhibited by self-expanding stents, balloon-expandable stents, and other medical devices as briefly discussed above. In addition, the present invention also overcomes the disadvantages associated with the potential loading effects caused by the interconnectedness of the structural members.

In accordance with one aspect, the present invention is directed to an intraluminal medical device. The intraluminal medical device comprises multiple, independent, self-expanding stent segments, each stent segment including a plurality of longitudinal struts, a plurality of loops connecting adjacent struts, at least one bridging element and at least one receptacle, wherein the at least one bridging element of one or more of the stent segments is configured to be releasably engaged with the at least one receptacle on an adjacent stent segment.

In accordance with another aspect, the present invention is directed to a delivery system for a segmented, self-expanding stent. The delivery system for a segmented, self-expanding stent comprising an outer sheath including an elongated tubular member having distal and proximal ends; and an inner shaft located coaxially and slidably within the outer sheath, the inner shaft having a distal end and a proximal end the shaft having a collar including mating sections for releasably securing at least a portion of the segmented, self-expanding stent.

Stent structures are often constructed of radially expanding members or hoops connected by bridge elements. In certain stent designs, the bridge elements may connect every tip or loop of the radially expanding members or hoops to a corresponding tip or loop of an adjacent radially expanding member or hoop. This type of design provides for a less flexible stent. In other stent designs, the bridge elements do not connect every set of tips or loops, but rather, the bridges are placed periodically. When bridges are periodically spaced, open gaps may exist between unconnected tips or loops. This design affords increased flexibility, however, potential deformation of the unconnected tips or loops may occur when the stent is subject to compressive axial loading, for example, during loading of the stent into the stent delivery system or during deployment of the stent. The anvil bridge design of the present invention may be utilized to effectively fill the gap between adjacent unconnected tips or loops without serving as a structural connection point between such tips or loops. Accordingly, there is no sacrifice in terms of flexibility.

In addition, the anvil bridge design serves to increase the surface area of the stent. This increased surface area may be utilized to modify a drug release profile by increasing the amount of drug available for drug delivery. Essentially, increased surface area on the stent allows for more drug coating thereon.

The intraluminal medical device of the present invention may utilize high radiopacity markers to ensure proper positioning of the device within a lumen. The markers comprise a housing which is integral to the device itself, thereby ensuring minimal interference with deployment and operation of the device. The housings are also shaped to minimally impact the overall profile of the stent. For example, a properly shaped housing allows a stent to maintain a radiopaque stent marker size utilized in a seven French delivery system to fit into a six French delivery system. The markers also comprise a properly sized marker insert having a higher radiopacity than the material forming the device itself. The marker insert is sized to match the curvature of the housing thereby ensuring a tight and unobtrusive fit. The marker inserts are made from a material close in the galvanic series to the device material and sized to substantially minimize the effect of galvanic corrosion.

The improved radiopacity intraluminal medical device of the present invention provides for more precise placement and post-procedural visualization in a lumen by increasing the radiopacity of the device under X-ray fluoroscopy. Given that the marker housings are integral to the device, they are simpler and less expensive to manufacture than markers that have to be attached in a separate process.

The improved radiopacity intraluminal medical device of the present invention is manufactured utilizing a process which ensures that the marker insert is securely positioned within the marker housing. The marker housing is laser cut from the same tube and is integral to the device. As a result of the laser cutting process, the hole in the marker housing is conical in the radial direction with the outer surface diameter being larger than the inner surface diameter. The conical tapering effect in the marker housing is beneficial in providing an interference fit between the marker insert and the marker housing to prevent the marker insert from being dislodged once the device is deployed. The marker inserts are loaded into a crimped device by punching a disk from annealed ribbon stock and shaping it to have the same radius of curvature as the marker housing. Once the disk is loaded into the marker housing, a coining process is used to properly seat the marker below the surface of the housing. The coining punch is also shaped to maintain the same radius of curvature as the marker housing. The coining process deforms the marker housing material to form a protrusion, thereby locking in the insert or disk.

In other embodiments, the intraluminal medical device of the present invention comprises a number of individual, independent, self-expanding stent segments which are designed to interlock when constrained within a delivery sheath and uncouple upon deployment. Since the elements are independent, there is no transmission of undesirable forces and/or loads.

The primary advantage of the independent stent structures is the ability to deploy individual segments in a controlled manner. The interlocking coupling may be designed such that it does not disengage a deployed segment from the delivery system until it is firmly opposed to the vessel wall. Without such a measure, short individual segments would tend to propel themselves out of the delivery system in an uncontrolled fashion as they expand to their full diameter.

Other advantages of the present invention includes providing the physician with the flexibility to tailor therapy to the target vessel disease state. Specifically, the length of the scaffolding may be precisely matched to the length of the lesion. Multiple lesions may be treated in a single intervention, using a single delivery device. Optionally, the pitch or spacing of the individual segments deployed at the treatment site may be varied to increase or decrease scaffolding density. Utilized in combination with drug eluting technology, this could also be used to alter drug dosage per unit length of vessel.

The delivery device may be pre-loaded with the maximum number of individual segments anticipated for a range of cases. As such, the same delivery system may be used to treat a short focal lesion or a long diffuse lesion. In the case of a short lesion, most of the pre-loaded stent segments may go unused and could be considered disposable.

Conventional stents are often comprised of expandable structural segments connected by bridges which join adjacent segments periodically around the circumference of the device. This system of unconnected, independent structural segments provides for an insensitivity to longitudinal elongation, compression or torsion. Essentially, without bridges to connect adjacent structural members, these structures will not be pulled or twisted if the vessel is elongated or twisted. This system also provides for an insensitivity to tortuosity. The short, independent segments will contour easily to conform to tortuous anatomy.

BRIEF DESCRIPTION OF THE DRAWINGS

The foregoing and other aspects of the present invention will best be appreciated with reference to the detailed description of the invention in conjunction with the accompanying drawings, wherein:

FIG. 9 is an enlarged perspective view of an end of the stent with the markers forming a substantially straight line in accordance with the present invention.

FIG. 10 is a simplified partial cross-sectional view of a stent delivery apparatus having a stent loaded therein, which can be used with a stent made in accordance with the present invention.

FIG. 11 is a view similar to that of FIG. 10 but showing an enlarged view of the distal end of the apparatus.

DETAILED DESCRIPTION OF THE PREFERRED EMBODIMENTS

Figure 1:
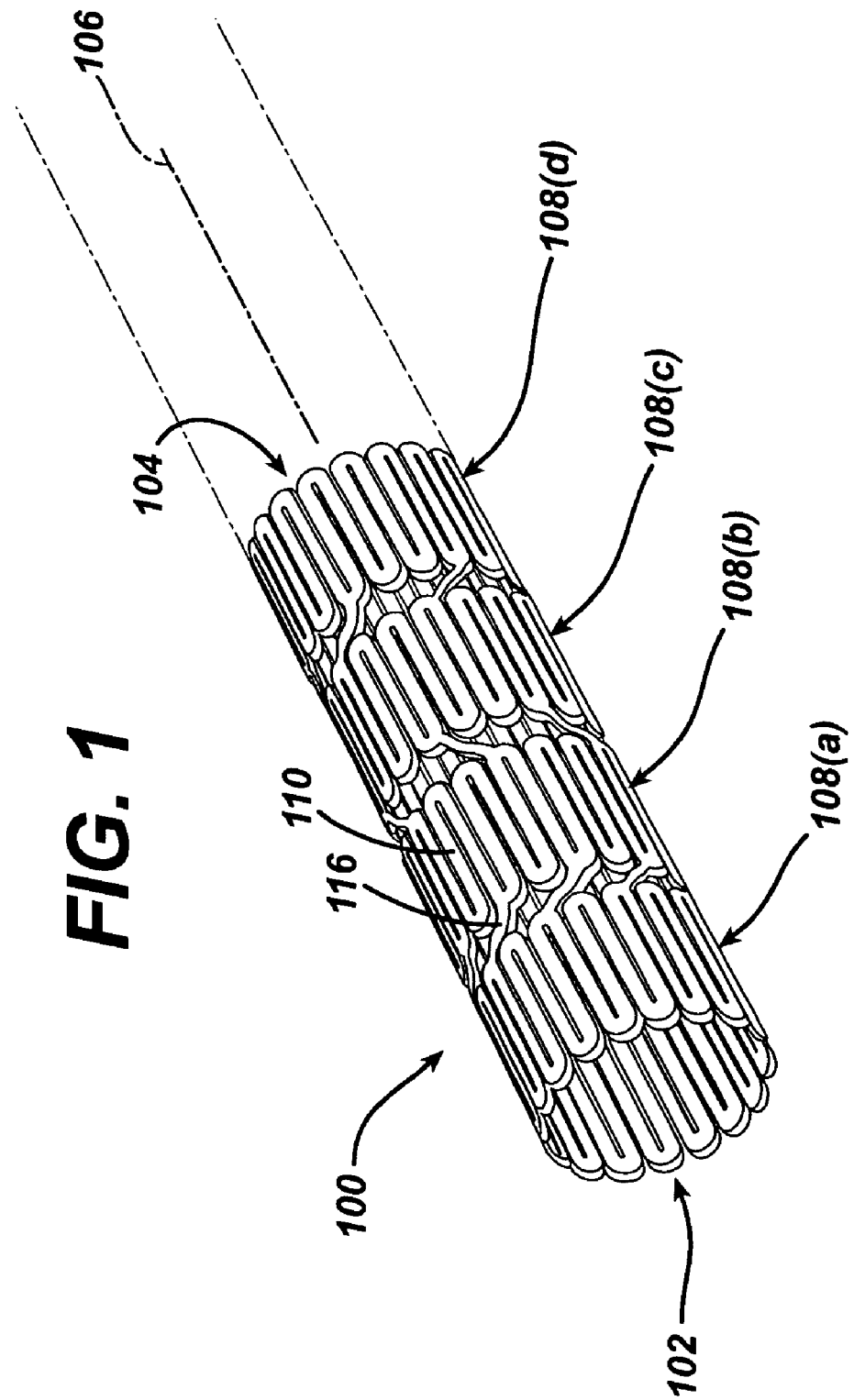
FIG. 1 is a perspective view of an exemplary stent in its compressed state which may be utilized in conjunction with the present invention.
Figure 2:
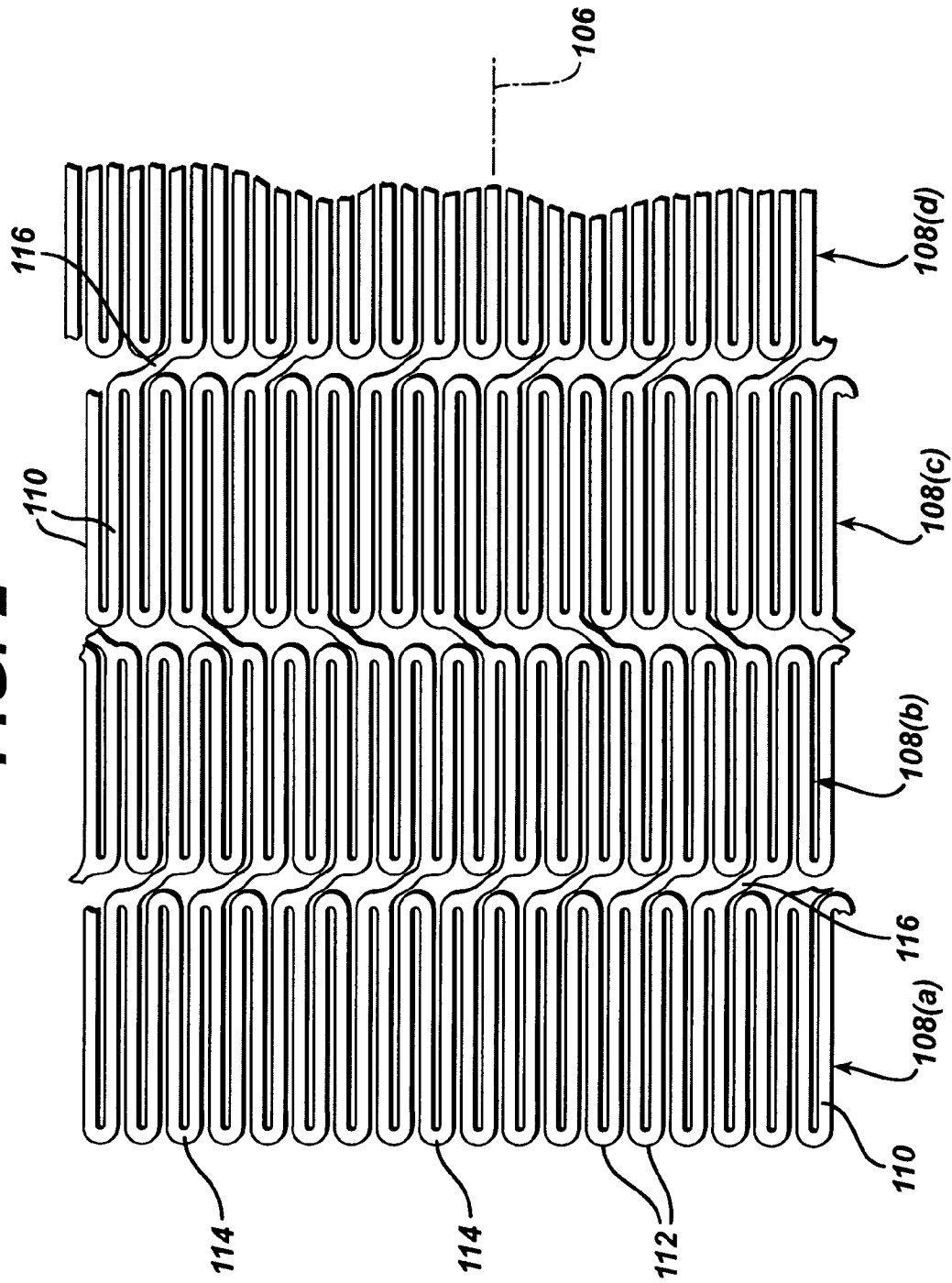
FIG. 2 is a sectional, flat view of the stent shown in FIG. 1.

While the present invention may be used on or in connection with any number of medical devices, including stents, for ease of explanation, one exemplary embodiment of the invention with respect to self-expanding Nitinol stents will be described in detail. There is illustrated in FIGS. 1 and 2, a stent 100, which may be utilized in connection with the present invention. FIGS. 1 and 2 illustrate the exemplary stent 100 in its unexpanded or compressed state. The stent 100 is preferably made from a superelastic alloy such as Nitinol. Most preferably, the stent 100 is made from an alloy comprising from about 50.0 percent (as used herein these percentages refer to weight percentages) Ni to about 60 percent Ni, and more preferably about 55.8 percent Ni, with the remainder of the alloy being Ti. Preferably, the stent 100 is designed such that it is superelastic at body temperature, and preferably has an Af in the range from about twenty-four degrees C. to about thirty-seven degrees C. The superelastic design of the stent 100 makes it crush recoverable, which, as discussed above, makes it useful as a stent or frame for any number of vascular devices in different applications.

Stent 100 is a tubular member having front and back open ends 102 and 104 and a longitudinal axis 106 extending therebetween. The tubular member has a first smaller diameter, FIGS. 1 and 2, for insertion into a patient and navigation through the vessels, and a second larger diameter, FIGS. 3 and 4, for deployment into the target area of a vessel. The tubular member is made from a plurality of adjacent hoops 108, FIG. 1 showing hoops 108(a)–108(d), extending between the front and back ends 102 and 104. The hoops 108 include a plurality of longitudinal struts 110 and a plurality of loops 112 connecting adjacent struts, wherein adjacent struts are connected at opposite ends so as to form a substantially S or Z shape pattern. The loops 112 are curved, substantially semi-circular with symmetrical sections about their centers 114.

Figure 5:
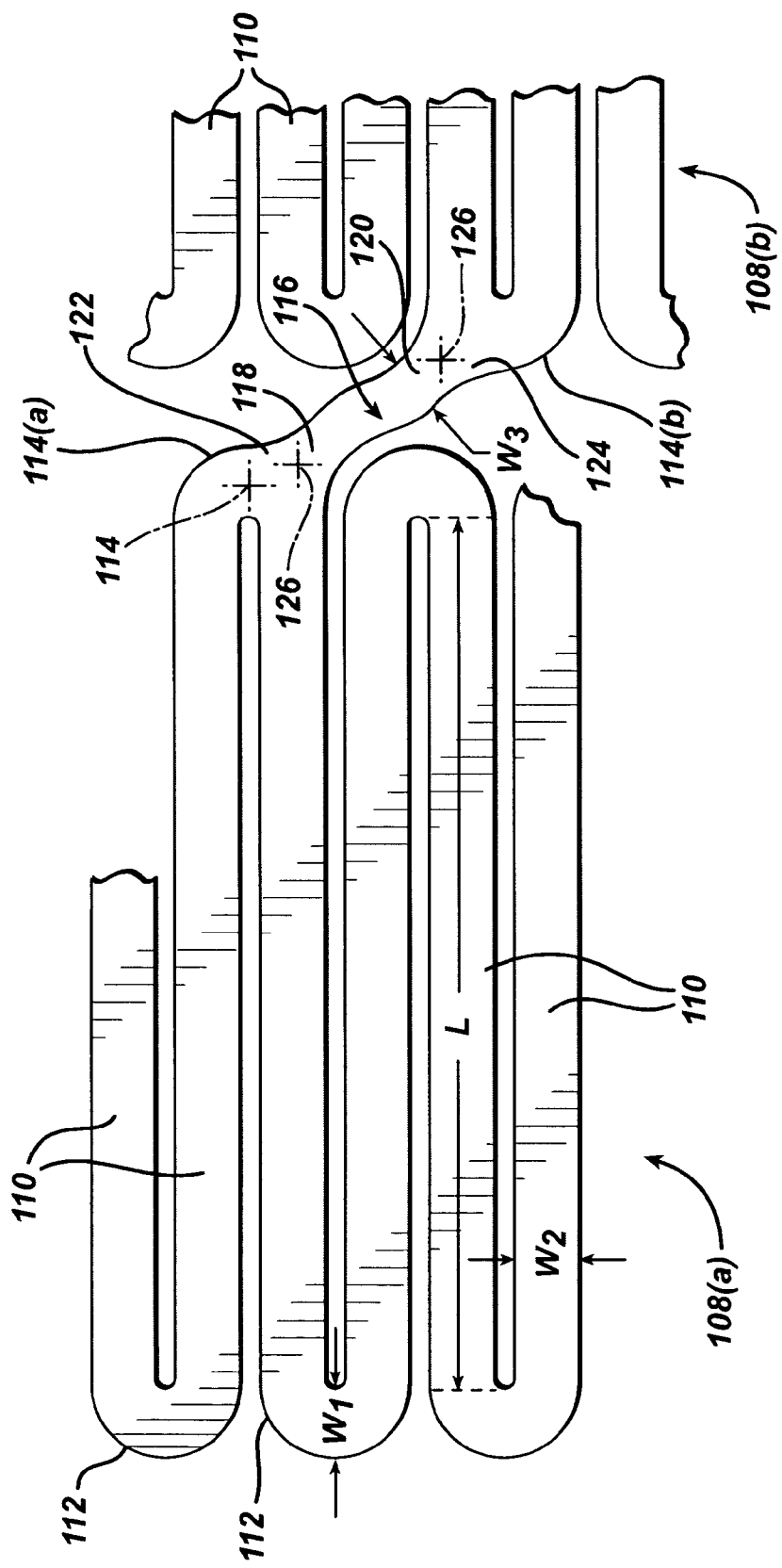
FIG. 5 is an enlarged view of section of the stent shown in FIG. 2.

Stent 100 further includes a plurality of bridges 116 which connect adjacent hoops 108 and which can best be described in detail by referring to FIG. 5. Each bridge 116 has two ends 118 and 120. The bridges 116 have one end attached to one strut and/or loop, and another end attached to a strut and/or loop on an adjacent hoop. The bridges 116 connect adjacent struts together at bridge to loop connection points 122 and 124. For example, bridge end 118 is connected to loop 114(a) at bridge to loop connection point 122, and bridge end 120 is connected to loop 114(b) at bridge to loop connection point 124. Each bridge to loop connection point has a center 126. The bridge to loop connection points are separated angularly with respect to the longitudinal axis. That is, the connection points are not immediately opposite each other. Essentially, one could not draw a straight line between the connection points, wherein such line would be parallel to the longitudinal axis of the stent.

The above-described geometry helps to better distribute strain throughout the stent, prevents metal-to-metal contact when the stent is bent, and minimizes the opening size between the struts, loops and bridges. The number of and nature of the design of the struts, loops and bridges are important factors when determining the working properties and fatigue life properties of the stent. It was previously thought that in order to improve the rigidity of the stent, that struts should be large, and therefore there should be fewer struts per hoop. However, it has now been discovered that stents having smaller struts and more struts per hoop actually improve the construction of the stent and provide greater rigidity. Preferably, each hoop has between twenty-four to thirty-six or more struts. It has been determined that a stent having a ratio of number of struts per hoop to strut length L (in inches) which is greater than four hundred has increased rigidity over prior art stents, which typically have a ratio of under two hundred. The length of a strut is measured in its compressed state parallel to the longitudinal axis 106 of the stent 100 as illustrated in FIG. 1.

Figure 3:
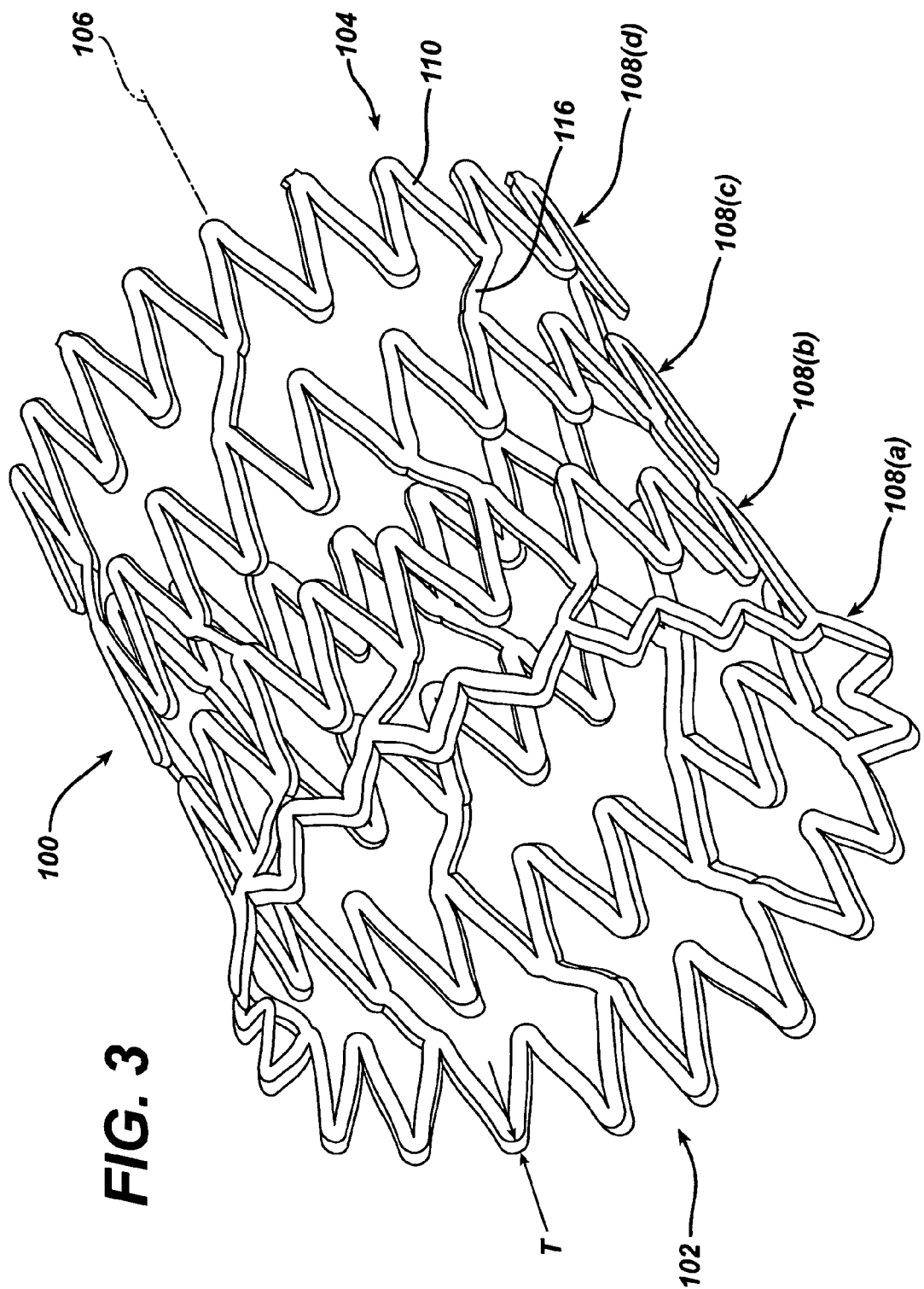
FIG. 3 is a perspective view of the stent shown in FIG. 1 but showing it in its expanded state.
Figure 4:
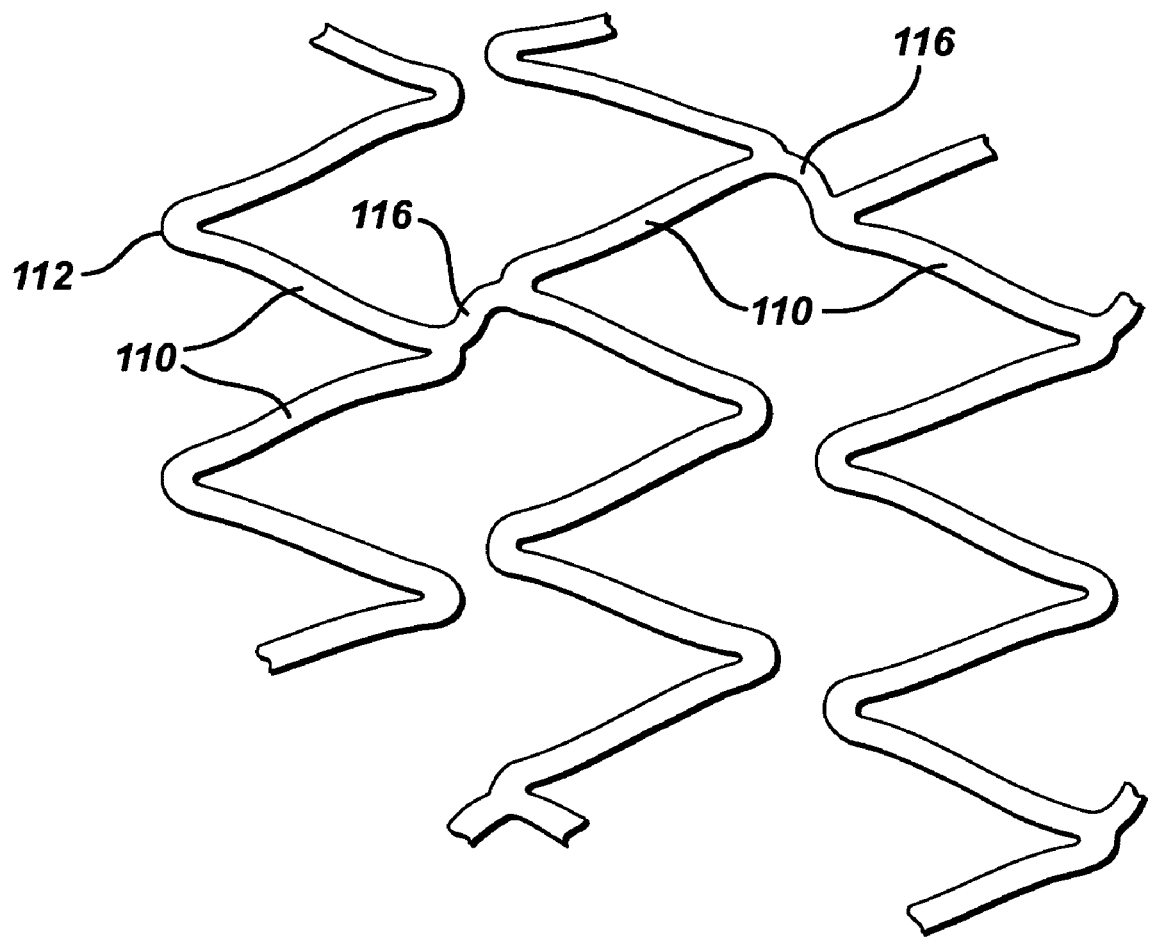
FIG. 4 is an enlarged sectional view of the stent shown in FIG. 3.

As seen from a comparison of FIGS. 2 and 3, the geometry of the stent 100 changes quite significantly as the stent 100 is deployed from its un-expanded state to its expanded state. As a stent undergoes diametric change, the strut angle and strain levels in the loops and bridges are affected. Preferably, all of the stent features will strain in a predictable manner so that the stent is reliable and uniform in strength. In addition, it is preferable to minimize the maximum strain experienced by struts loops and bridges, since Nitinol properties are more generally limited by strain rather than by stress. As will be discussed in greater detail below, the stent sits in the delivery system in its un-expanded state as shown in FIGS. 10 and 11. As the stent is deployed, it is allowed to expand towards its expanded state, as shown in FIG. 3, which preferably has a diameter which is the same or larger than the diameter of the target vessel. Nitinol stents made from wire deploy in much the same manner, and are dependent upon the same design constraints, as laser cut stents. Stainless steel stents deploy similarly in terms of geometric changes as they are assisted by forces from balloons or other devices.

In trying to minimize the maximum strain experienced by features of the stent, the present invention utilizes structural geometries which distribute strain to areas of the stent which are less susceptible to failure than others. For example, one of the most vulnerable areas of the stent is the inside radius of the connecting loops. The connecting loops undergo the most deformation of all the stent features. The inside radius of the loop would normally be the area with the highest level of strain on the stent. This area is also critical in that it is usually the smallest radius on the stent. Stress concentrations are generally controlled or minimized by maintaining the largest radii possible. Similarly, we want to minimize local strain concentrations on the bridge and bridge connection points. One way to accomplish this is to utilize the largest possible radii while maintaining feature widths which are consistent with applied forces. Another consideration is to minimize the maximum open area of the stent. Efficient utilization of the original tube from which the stent is cut increases stent strength and its ability to trap embolic material.

Many of these design objectives have been accomplished by an exemplary embodiment of the present invention, illustrated in FIGS. 1, 2 and 5. As seen from these figures, the most compact designs which maintain the largest radii at the loop to bridge connections are non-symmetric with respect to the centerline of the strut connecting loop. That is, loop to bridge connection point centers 126 are offset from the center 114 of the loops 112 to which they are attached. This feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. This feature allows for maximum utilization of Ni—Ti or other material properties to enhance radial strength, to improve stent strength uniformity, to improve fatigue life by minimizing local strain levels, to allow for smaller open areas which enhance entrapment of embolic material, and to improve stent apposition in irregular vessel wall shapes and curves.

As seen in FIG. 5, stent 100 comprises strut connecting loops 112 having a width W1, as measured at the center 114 parallel to axis 106, which are greater than the strut widths W2, as measured perpendicular to axis 106 itself. In fact, it is preferable that the thickness of the loops vary so that they are thickest near their centers. This increases strain deformation at the strut and reduces the maximum strain levels at the extreme radii of the loop. This reduces the risk of stent failure and allows one to maximize radial strength properties. This feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. As stated above, this feature allows for maximum utilization of Ni—Ti or other material properties to enhance radial strength, to improve stent strength uniformity, to improve fatigue life by minimizing local strain levels, to allow for smaller open areas which enhance entrapment of embolic material, and to improve stent apposition in irregular vessel wall shapes and curves.

As mentioned above, bridge geometry changes as a stent is deployed from its compressed state to its expanded state and vise-versa. As a stent undergoes diametric change, strut angle and loop strain is affected. Since the bridges are connected to either the loops, struts or both, they are affected. Twisting of one end of the stent with respect to the other, while loaded in the stent delivery system, should be avoided. Local torque delivered to the bridge ends displaces the bridge geometry. If the bridge design is duplicated around the stent perimeter, this displacement causes rotational shifting of the two loops being connected by the bridges. If the bridge design is duplicated throughout the stent, as in the present invention, this shift will occur down the length of the stent. This is a cumulative effect as one considers rotation of one end with respect to the other upon deployment. A stent delivery system, such as the one described below, will deploy the distal end first, then allow the proximal end to expand. It would be undesirable to allow the distal end to anchor into the vessel wall while holding the stent fixed in rotation, then release the proximal end. This could cause the stent to twist or whip in rotation to equilibrium after it is at least partially deployed within the vessel. Such whipping action may cause damage to the vessel.

However, one exemplary embodiment of the present invention, as illustrated in FIGS. 1 and 2, reduces the chance of such events happening when deploying the stent. By mirroring the bridge geometry longitudinally down the stent, the rotational shift of the Z-sections or S-sections may be made to alternate and will minimize large rotational changes between any two points on a given stent during deployment or constraint. That is, the bridges 116 connecting loop 108(*b*) to loop 108(*c*) are angled upwardly from left to right, while the bridges connecting loop 108(*c*) to loop 108(*d*) are angled downwardly from left to right. This alternating pattern is repeated down the length of the stent 100. This alternating pattern of bridge slopes improves the torsional characteristics of the stent so as to minimize any twisting or rotation of the stent with respect to any two hoops. This alternating bridge slope is particularly beneficial if the stent starts to twist in vivo. As the stent twists, the diameter of the stent will change. Alternating bridge slopes tend to minimize this effect. The diameter of a stent having bridges which are all sloped in the same direction will tend to grow if twisted in one direction and shrink if twisted in the other direction. With alternating bridge slopes this effect is minimized and localized.

Preferably, stents are laser cut from small diameter tubing. For prior art stents, this manufacturing process led to designs with geometric features, such as struts, loops and bridges, having axial widths W2, W1 and W3, respectively, which are larger than the tube wall thickness T (illustrated in FIG. 3). When the stent is compressed, most of the bending occurs in the plane that is created if one were to cut longitudinally down the stent and flatten it out. However, for the individual bridges, loops and struts, which have widths greater than their thickness, there is a greater resistance to this in-plane bending than to out-of-plane bending. Because of this, the bridges and struts tend to twist, so that the stent as a whole may bend more easily. This twisting is a buckling condition which is unpredictable and can cause potentially high strain.

However, this problem has been solved in an exemplary embodiment of the present invention, as illustrated in FIGS. 1–5. As seen from these figures, the widths of the struts, hoops and bridges are equal to or less than the wall thickness of the tube. Therefore, substantially all bending and, therefore, all strains are "out-of-plane." This minimizes twisting of the stent which minimizes or eliminates buckling and unpredictable strain conditions. This feature is particularly advantageous for stents having large expansion ratios, which in turn requires them to have extreme bending requirements where large elastic strains are required. Nitinol, as stated above, can withstand extremely large amounts of elastic strain deformation, so the above features are well suited to stents made from this alloy. This feature allows for maximum utilization of Ni—Ti or other material properties to enhance radial strength, to improve stent strength uniformity, to improve fatigue life by minimizing local strain levels, to allow for smaller open areas which enhance entrapment of embolic material, and to improve stent apposition in irregular vessel wall shapes and curves.

Figure 6:
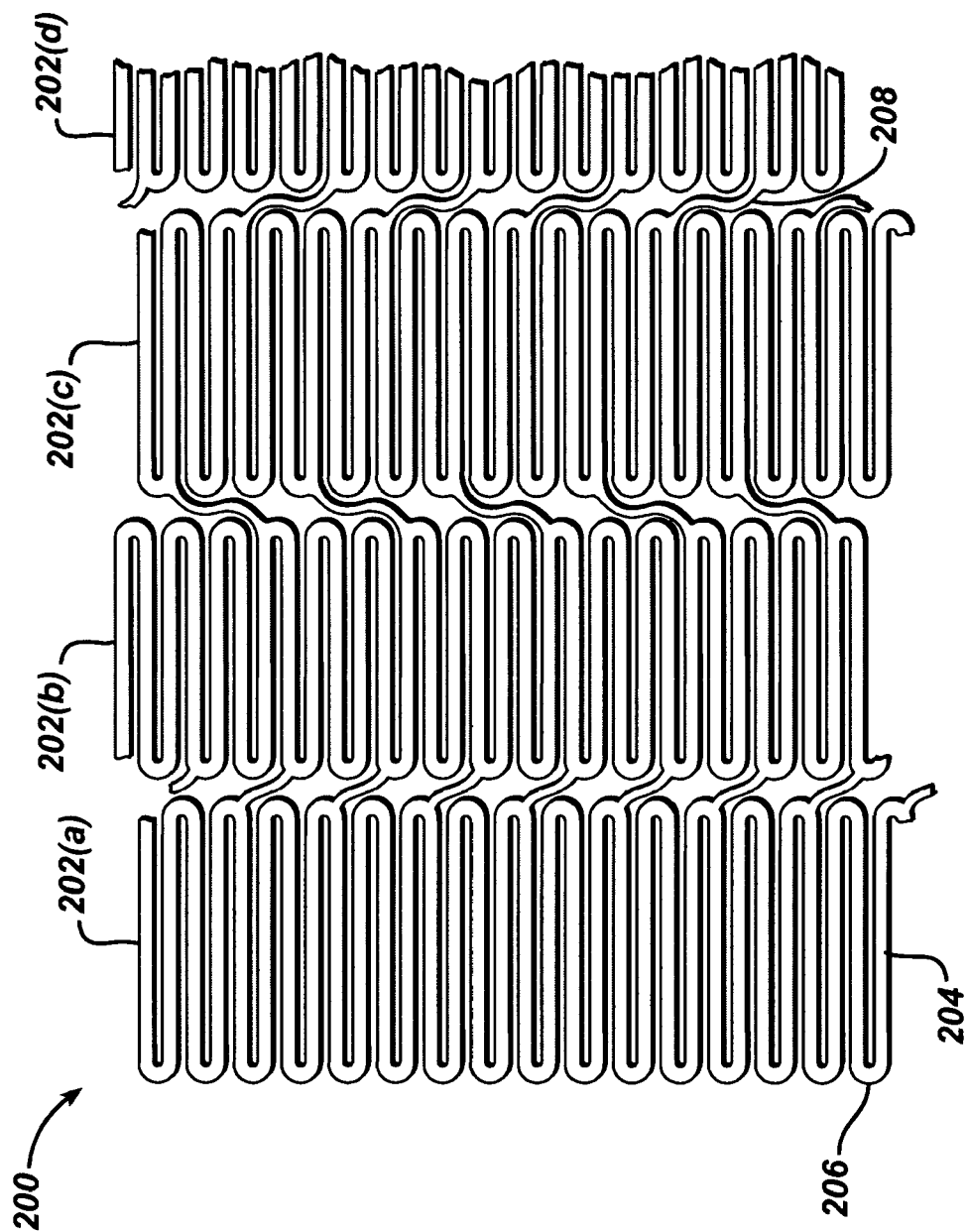
FIG. 6 is a view similar to that of FIG. 2 but showing an alternate embodiment of the stent.

An alternate exemplary embodiment of a stent that may be utilized in conjunction with the present invention is illustrated in FIG. 6. FIG. 6 shows stent 200 which is similar to stent 100 illustrated in FIGS. 1–5. Stent 200 is made from a plurality of adjacent hoops 202, FIG. 6 showing hoops 202(a)–202(d). The hoops 202 include a plurality of longitudinal struts 204 and a plurality of loops 206 connecting adjacent struts, wherein adjacent struts are connected at opposite ends so as to form a substantially S or Z shape pattern. Stent 200 further includes a plurality of bridges 208 which connect adjacent hoops 202. As seen from the figure, bridges 208 are non-linear and curve between adjacent hoops. Having curved bridges allows the bridges to curve around the loops and struts so that the hoops can be placed closer together which in turn, minimizes the maximum open area of the stent and increases its radial strength as well. This can best be explained by referring to FIG. 4. The above described stent geometry attempts to minimize the largest circle which could be inscribed between the bridges, loops and struts, when the stent is expanded. Minimizing the size of this theoretical circle greatly improves the stent because it is then better suited to provide consistent scaffolding support to support the vessel and trap embolic material once it is inserted into the patient.

As mentioned above, it is preferred that the stent of the present invention be made from a superelastic alloy and most preferably made of an alloy material having greater than 50.5 atomic percentage Nickel and the balance Titanium. Greater than 50.5 atomic percentage Nickel allows for an alloy in which the temperature at which the martensite phase transforms completely to the austenite phase (the Af temperature) is below human body temperature, and preferably is about twenty-four degrees C. to about thirty-seven degrees C., so that austenite is the only stable phase at body temperature.

In manufacturing the Nitinol stent, the material is first in the form of a tube. Nitinol tubing is commercially available from a number of suppliers including Nitinol Devices and Components, Fremont Calif. The tubular member is then loaded into a machine which will cut the predetermined pattern of the stent into the tube, as discussed above and as shown in the figures. Machines for cutting patterns in tubular devices to make stents or the like are well known to those of ordinary skill in the art and are commercially available. Such machines typically hold the metal tube between the open ends while a cutting laser, preferably under microprocessor control, cuts the pattern. The pattern dimensions and styles, laser positioning requirements, and other information are programmed into a microprocessor, which controls all aspects of the process. After the stent pattern is cut, the stent is treated and polished using any number of methods or combination of methods well known to those skilled in the art. Lastly, the stent is then cooled until it is completely martensitic, crimped down to its un-expanded diameter and then loaded into the sheath of the delivery apparatus.

Figure 15:
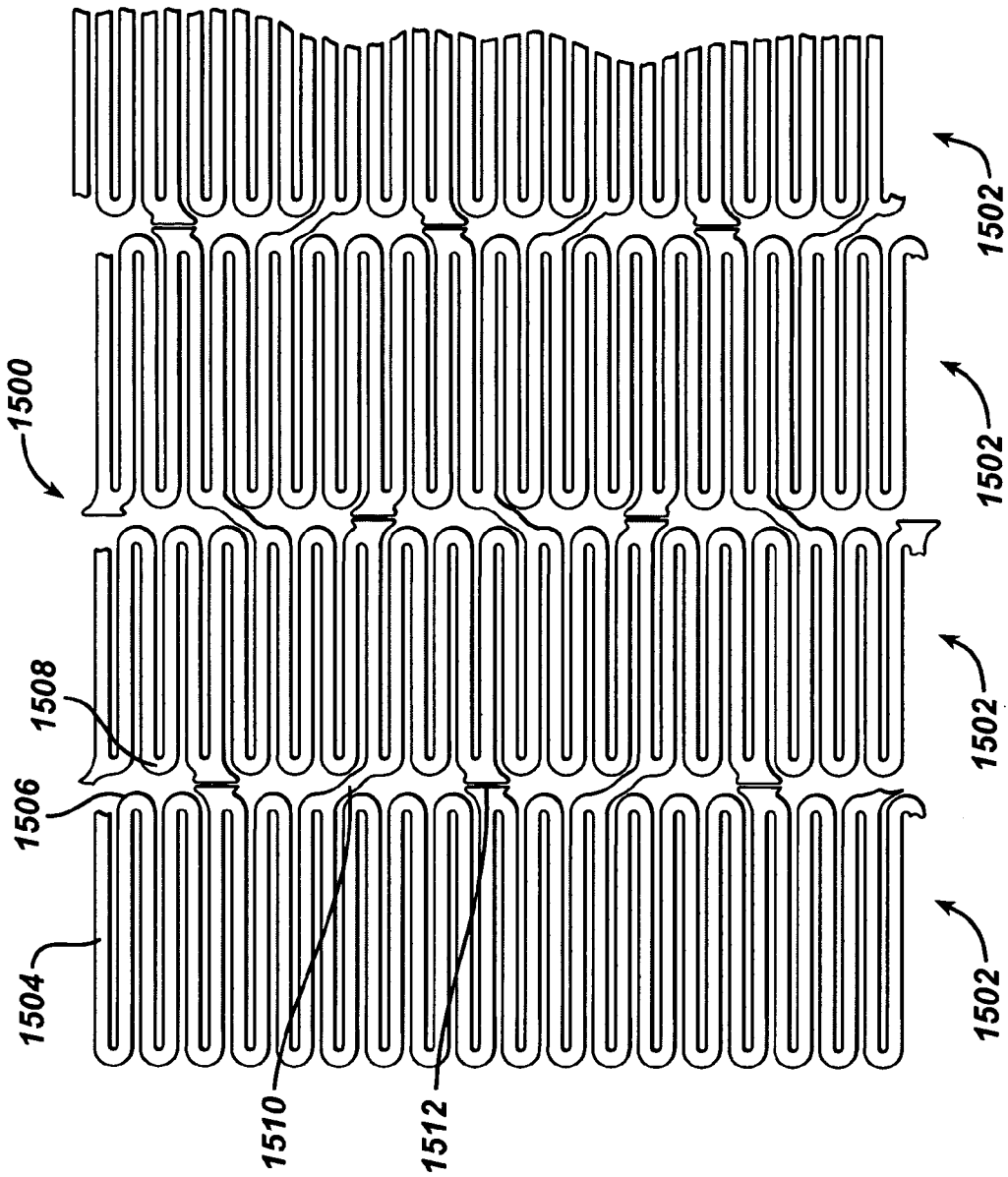
FIG. 15 is a sectional, flat view of an exemplary embodiment of a split-bridge stent in accordance with the present invention.

FIG. 15 illustrates an alternate exemplary embodiment of a self-expanding stent 1500 formed from Nitinol. In this exemplary embodiment, a plurality of split-bridges are utilized to fill the gap between unbridged loops without serving as a structural connection point between these loops. In stent designs featuring periodically placed bridges, as is described herein, the resulting gaps between unconnected loops may be disadvantageous, especially during loading of the stent into a stent delivery system and subsequent deployment from a stent delivery system. In both the loading and deployment situations, the stent is constrained to a small diameter and subjected to high compressive axial forces. These forces are transmitted axially through the stent by the connecting bridges and may cause undesirable buckling or compression of the adjacent hoops in the areas where the loops are not connected by bridges. A split-bridge may be utilized to substantially minimize this undesirable deformation under conditions of constrained axial compression. Essentially, when a stent, having split-bridges is constrained and subjected to axial compression, the wide flat surfaces of adjacent ends of the split-bridge, as is explained in detail subsequently, quickly come into contact and transmit compressive axial loads without allowing undesirable deformation of the stent structure. The split-bridge design is particularly advantageous in that it allows the transmission of the compressive axial loads during stent loading and deployment without the loss of flexibility caused by standard bridges once the stent is deployed.

A simple example may be utilized to illustrate the usefulness of a stent comprising split-bridges. A constrained stent which comprises three bridges, typically spaced one hundred twenty degrees apart, must transmit the entire compressive load associated with stent loading and deployment through these three bridges. Unconnected loops within the one hundred twenty degree arc or span between bridges may be undesirably deformed, potentially out of plane, thereby allowing compression of the entire stent structure and potentially adversely impacting loading or deployment characteristics. However, a stent with three standard bridges and three split-bridges would better distribute the axial compressive load, with half the load at or on each bridge, now spaced apart by sixty degrees. In this scenario, there are fewer unconnected loops within the sixty-degree arc or span and these loops would be less likely to become undesirably deformed when the structure is subject to compressive axial loads. Essentially, by allowing efficient transmission of compressive axial loads, the split-bridge helps to prevent undesirable compression or deformation of the constrained stent and loading or deployment difficulties, which may result from such compression or deformation. This may facilitate loading and delivery of stent designs which might otherwise be impractical.

It is important to note that symmetric loading and hence symmetric placement of the bridges is preferable but not necessary.

Although the split-bridge design may be utilized in any number of stent designs, for ease of explanation, the split-bridge design is described with respect to the exemplary stent illustrated in FIG. 15. As illustrated, the stent 1500 comprises a plurality of adjacent hoops 1502. The hoops 1502 include a plurality of longitudinal struts 1504 and a plurality of loops 1506 connecting adjacent struts 1504, wherein adjacent struts 1504 are connected at opposite ends so as to form a substantially S or Z shape pattern. The loops 1506 are curved, substantially semi-circular with symmetrical sections about their centers 1508. The stent 1500 further comprises a plurality of bridges 1510 which connect adjacent hoops 1502. The bridges 1510 are equivalent to the bridges illustrated in FIG. 5 and described above. Also as described above, the bridge orientation is changed from hoop to hoop so as to minimize rotational changes between any two points on a given stent during stent deployment or constraint. The number of and nature of the design of the struts, loops and bridges are important factors when determining the working properties and fatigue life properties of the stent as is discussed above.

The stent 1500 also comprises a plurality of split-bridges 1512. The split-bridges 1512 may comprise any suitable configuration and may be positioned in any suitable pattern between bridges 1510. In the exemplary embodiment illustrated in FIG. 15, the split-bridges 1512 are orientated in a direction opposite from that of the bridges 1510 such that a symmetric configuration of bridges 1510 and split-bridges 1512 results. As stated above, a symmetric configuration is not required, but it is preferred. Unlike the bridge 1510 design, the split-bridges 1512 is designed to maximize the surface area for contact between adjacent sections of the split-bridges 1512. This split-bridge design allows for contact between adjacent sections and thus force transmission even if the adjacent hoops 1502 become somewhat misaligned. The width or thickness of the split-bridges 1512 is preferably larger than the width or thickness of the standard bridges 1510 to provide additional surface area for abutting contact. Similarly to bridges 1510, the split-bridges 1512 have one end of one independent section attached to the one loop 1506 and another end of one independent section attached to a loop 1506 on an adjacent hoop 1502. Essentially, each split-bridge 1512 comprises first and second independent sections which come into contact when the stent 1500 is under compressive axial loading and make no contact when the stent 1500 is deployed.

The geometry of the split-bridge may take any number of forms which serves the purpose of filling the gaps which may be unoccupied by standard bridges. In addition, the number and arrangement of split-bridges is virtually unlimited.

Figure 16:
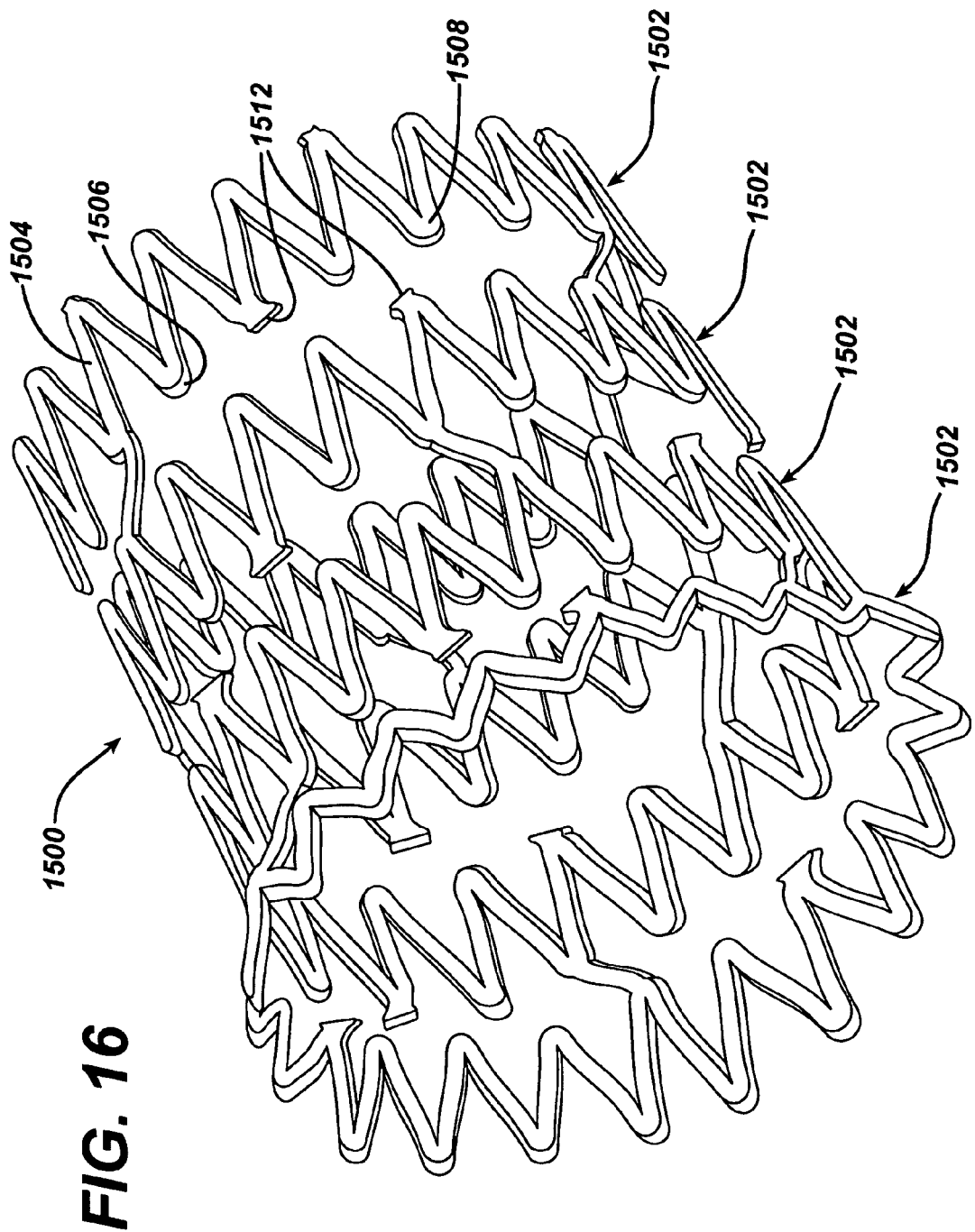
FIG. 16 is a perspective view of the stent illustrated in FIG. 15, but showing the stent in the expanded state.

By its nature, the split-bridge advantageously allows transmission of compressive loads when constrained because the sections of each split-bridge abut at least partially. However, unlike a traditional bridge, it does not transmit tensile or compressive strains when the expanded structure is stretched, compressed or bent. As illustrated in FIG. 16, the split-bridges are not aligned once the structure is expanded. As such, the split-bridge may prove advantageous over a traditional bridge in contourability and fatigue durability.

Various drugs, agents or compounds may be locally delivered via medical devices such as stents. For example, rapamycin and/or heparin may be delivered by a stent to reduce restenosis, inflammation and coagulation. One potential limiting factor in these stents is the surface area available on the stent for the drugs, agents and/or compounds. Accordingly, in addition to the advantages discussed above, the split-bridge offers additional surface area onto which various drugs, agents and/or compounds may be affixed.

Figure 7:
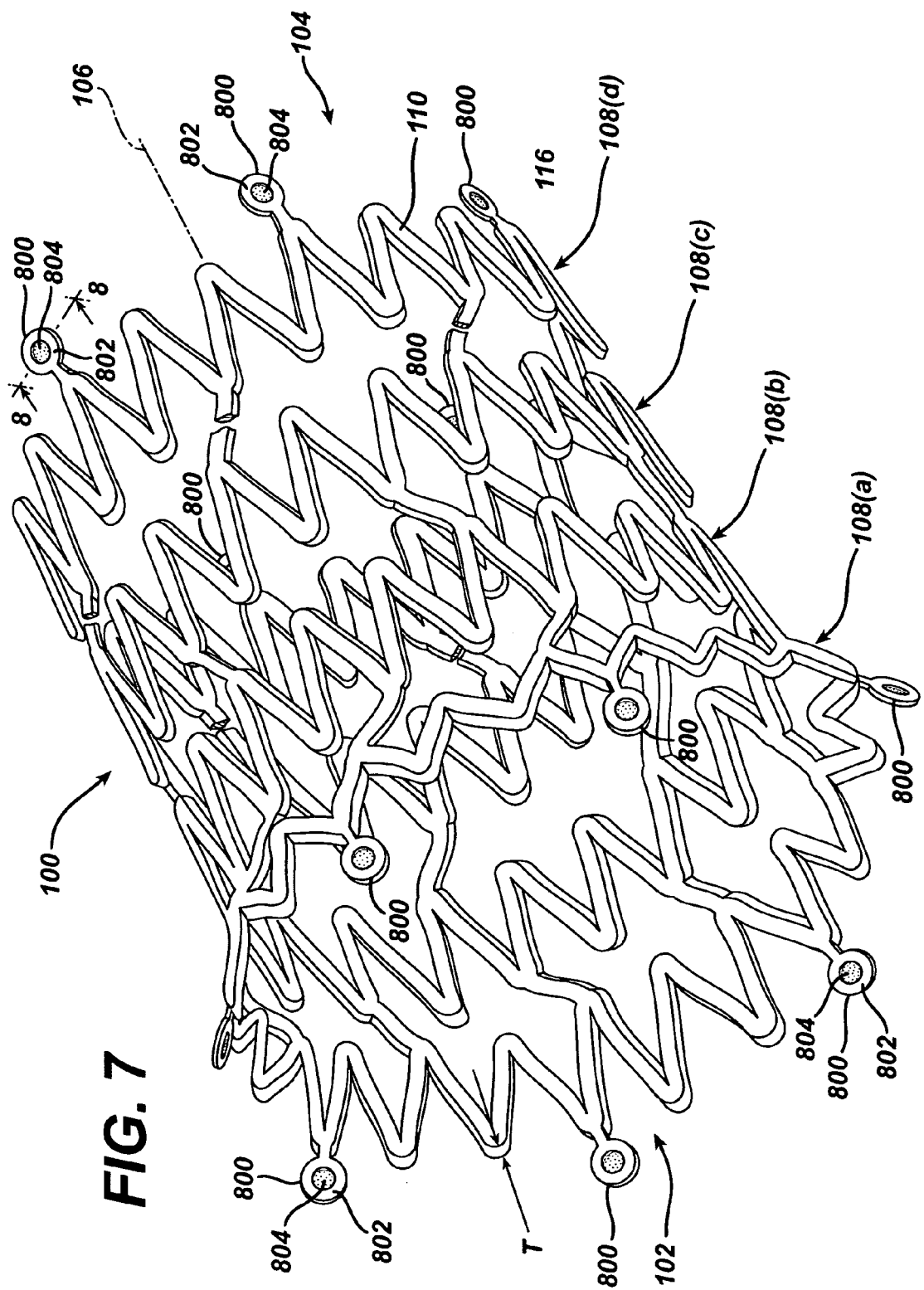
FIG. 7 is a perspective view of the stent of FIG. 1 having a plurality of markers attached to the ends thereof in accordance with the present invention.
Figure 8:
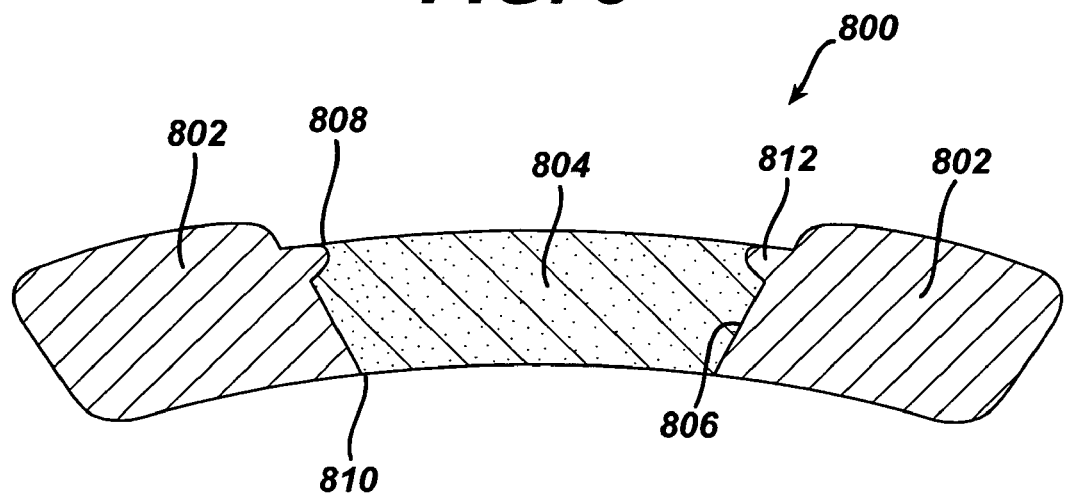
FIG. 8 is a cross-sectional view of a marker in accordance with the present invention.

As stated in previous sections of this application, markers having a radiopacity greater than that of the superelastic alloys may be utilized to facilitate more precise placement of the stent within the vasculature. In addition, markers may be utilized to determine when and if a stent is fully deployed. For example, by determining the spacing between the markers, one can determine if the deployed stent has achieved its maximum diameter and adjusted accordingly utilizing a tacking process. FIG. 7 illustrates an exemplary embodiment of the stent 100 illustrated in FIGS. 1–5 having at least one marker on each end thereof. In a preferred embodiment, a stent having thirty-six struts per hoop can accommodate six markers 800. Each marker 800 comprises a marker housing 802 and a marker insert 804. The marker insert 804 may be formed from any suitable biocompatible material having a high radiopacity under X-ray fluoroscopy. In other words, the marker inserts 804 should preferably have a radiopacity higher than that of the material comprising the stent 100. The addition of the marker housings 802 to the stent necessitates that the lengths of the struts in the last two hoops at each end of the stent 100 be longer than the strut lengths in the body of the stent to increase the fatigue life at the stent ends. The marker housings 802 are preferably cut from the same tube as the stent as briefly described above. Accordingly, the housings 802 are integral to the stent 100. Having the housings 802 integral to the stent 100 serves to ensure that the markers 800 do not interfere with the operation of the stent FIG. 8 is a cross-sectional view of a marker housing 802. The housing 802 may be elliptical when observed from the outer surface as illustrated in FIG. 7. As a result of the laser cutting process, the hole 806 in the marker housing 802 is conical in the radial direction with the outer surface 808 having a diameter larger than the diameter of the inner surface 810, as illustrated in FIG. 8. The conical tapering in the marker housing 802 is beneficial in providing an interference fit between the marker insert 804 and the marker housing 802 to prevent the marker insert 804 from being dislodged once the stent 100 is deployed. A detailed description of the process of locking the marker insert 804 into the marker housing 802 is given below.

As set forth above, the marker inserts 804 may be made from any suitable material having a radiopacity higher than the superelastic material forming the stent or other medical device. For example, the marker insert 804 may be formed from niobium, tungsten, gold, platinum or tantalum. In the preferred embodiment, tantalum is utilized because of its closeness to nickel-titanium in the galvanic series and thus would minimize galvanic corrosion. In addition, the surface area ratio of the tantalum marker inserts 804 to the nickel-titanium is optimized to provide the largest possible tantalum marker insert, easy to see, while minimizing the galvanic corrosion potential. For example, it has been determined that up to nine marker inserts 804 having a diameter of 0.010 inches could be placed at the end of the stent 100; however, these marker inserts 804 would be less visible under X-ray fluoroscopy. On the other hand, three to four marker inserts 804 having a diameter of 0.025 inches could be accommodated on the stent 100; however, galvanic corrosion resistance would be compromised. Accordingly, in the preferred embodiment, six tantalum markers having a diameter of 0.020 inches are utilized on each end of the stent 100 for a total of twelve markers 800.

The tantalum markers 804 may be manufactured and loaded into the housing utilizing a variety of known techniques. In the exemplary embodiment, the tantalum markers 804 are punched out from an annealed ribbon stock and are shaped to have the same curvature as the radius of the marker housing 802 as illustrated in FIG. 8. Once the tantalum marker insert 804 is loaded into the marker housing 802, a coining process is used to properly seat the marker insert 804 below the surface of the housing 802. The coining punch is also shaped to maintain the same radius of curvature as the marker housing 802. As illustrated in FIG. 8, the coining process deforms the marker housing 802 material to lock in the marker insert 804.

As stated above, the hole 806 in the marker housing 802 is conical in the radial direction with the outer surface 808 having a diameter larger than the diameter of the inner surface 810 as illustrated in FIG. 8. The inside and outside diameters vary depending on the radius of the tube from which the stent is cut. The marker inserts 804, as stated above, are formed by punching a tantalum disk from annealed ribbon stock and shaping it to have the same radius of curvature as the marker housing 802. It is important to note that the marker inserts 804, prior to positioning in the marker housing 804, have straight edges. In other words, they are not angled to match the hole 806. The diameter of the marker insert 804 is between the inside and outside diameter of the marker housing 802. Once the marker insert 804 is loaded into the marker housing 802, a coining process is used to properly seat the marker insert 804 below the surface of the marker housing 802. In the preferred embodiment, the thickness of the marker insert 804 is less than or equal to the thickness of the tubing and thus the thickness or height of the hole 806. Accordingly, by applying the proper pressure during the coining process and using a coining tool that is larger than the marker insert 804, the marker insert 804 may be seated in the marker housing 802 in such a way that it is locked into position by a radially oriented protrusion 812. Essentially, the applied pressure, and size and shape of the housing tool forces the marker insert 804 to form the protrusion 812 in the marker housing 802. The coining tool is also shaped to maintain the same radius of curvature as the marker housing 802. As illustrated in FIG. 8, the protrusion 812 prevents the marker insert 804 from becoming dislodged from the marker housing 802.

It is important to note that the marker inserts 804 are positioned in and locked into the marker housing 802 when the stent 100 is in its unexpanded state. This is due to the fact that it is desirable that the tube's natural curvature be utilized. If the stent were in its expanded state, the coining process would change the curvature due to the pressure or force exerted by the coining tool.

As illustrated in FIG. 9, the marker inserts 804 form a substantially solid line that clearly defines the ends of the stent in the stent delivery system when seen under fluoroscopic equipment. As the stent 100 is deployed from the stent delivery system, the markers 800 move away from each other and flower open as the stent 100 expands as illustrated in FIG. 7. The change in the marker grouping provides the physician or other health care provider with the ability to determine when the stent 100 has been fully deployed from the stent delivery system.

It is important to note that the markers 800 may be positioned at other locations on the stent 100.

Figure 12:
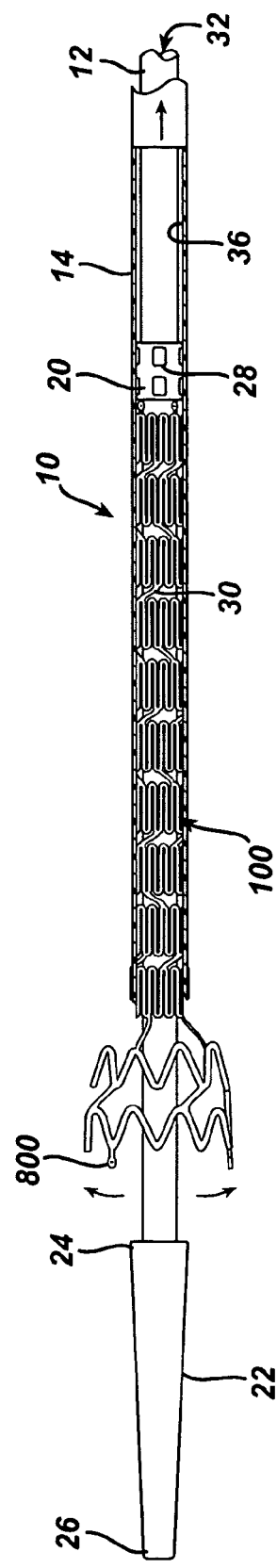
FIG. 12 is a perspective view of an end of the stent with the markers in a partially expanded form as it emerges from the delivery apparatus in accordance with the present invention.
Figure 13:
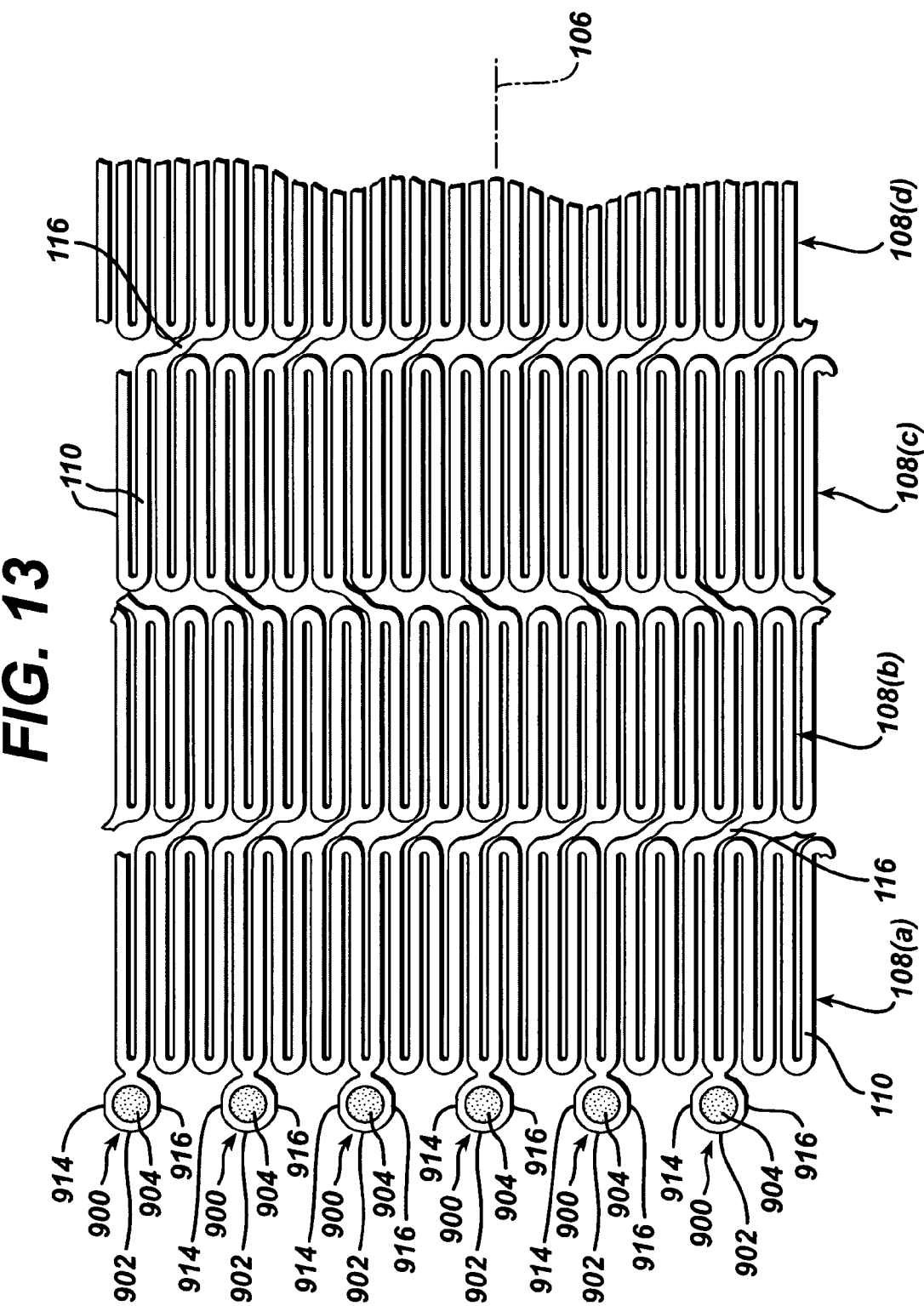
FIG. 13 is an enlarged perspective view of an end of the stent with modified markers in accordance with an alternate exemplary embodiment of the present invention.

FIG. 13 illustrates an alternate exemplary embodiment of a radiopaque marker 900. In this exemplary embodiment, the marker housing 902 comprises flat sides 914 and 916. The flat sides 914 and 916 serve a number of functions. Firstly, the flat sides 914 and 916 minimize the overall profile of the stent 100 without reducing the radiopacity of the stent 100 under x-ray fluoroscopy. Essentially, the flat sides 914 and 916 allow the marker housings 902 to fit more closely together when the stent 100 is crimped for delivery. Accordingly, the flat sides 914 and 916 of the marker housing 902 allow for larger stents to utilize high radiopacity markers while also allowing the stent to fit into smaller delivery systems. For example, the flat sides 914 and 916 on radiopaque markers 900 of the size described above (i.e. having appropriately sized markers) allow a stent to maintain a radiopaque stent marker size utilized in a seven French delivery system to fit into a six French delivery system. Secondly, the flat sides 914 and 916 also maximize the nitinol tab to radiopaque marker material ratio, thereby further reducing the effects of any galvanic corrosion as described above. The marker insert 904 and the marker hole 906 are formed of the same materials and have the same shape as described above with respect to FIGS. 1–12. The markers 900 are also constructed utilizing the same coining process as described above.

Figure 14:
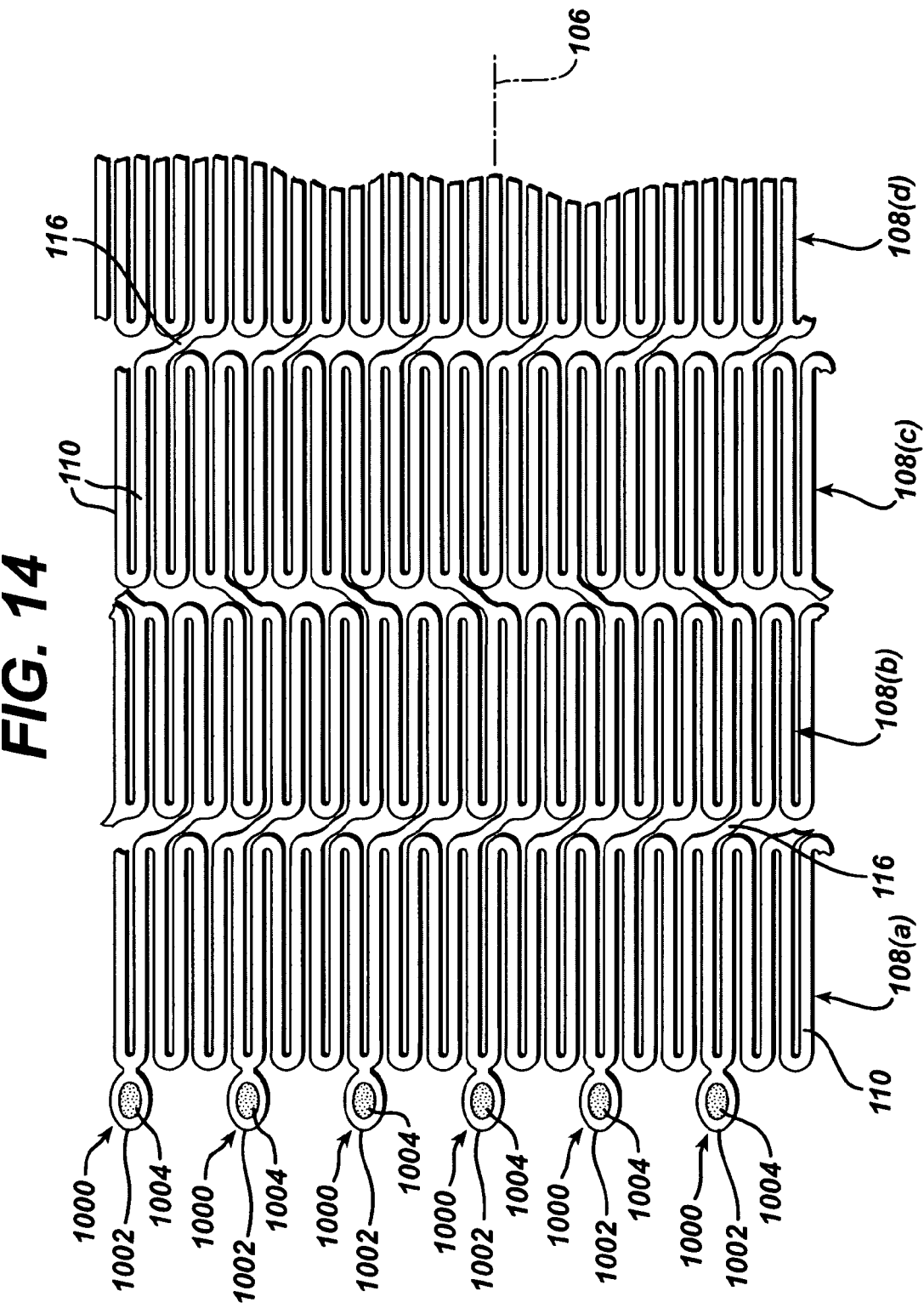
FIG. 14 is an enlarged perspective view of an end of the stent with modified markers in accordance with another alternate exemplary embodiment of the present invention.

FIG. 14 illustrates yet another alternate exemplary embodiment of a radiopaque marker 1000. This exemplary embodiment offers the same advantages as the above-described embodiment; namely, reduced profile without reduction in radiopacity and a reduction in the effects of galvanic corrosion. In this exemplary embodiment, the radiopaque marker 1000 has substantially the same total area as that of the markers 900, 800 described above, but with an oval shape rather than a circular shape or circular shape with flat sides. As illustrated, the marker 1000 comprises a substantially oval shaped marker housing 1002 and a substantially oval shaped marker insert 1004. Essentially, in this exemplary embodiment, the marker 1000 is longer in the axial direction and shorter in the radial direction to allow a larger stent to fit into a smaller delivery system as described above. Also as in the above-described exemplary embodiment, the nitinol tab to radiopaque marker material ratio is improved. In addition, the substantially oval shape provides for a more constant marker housing 1002 thickness around the marker insert 1004. Once again, the markers 1000 are constructed from the same materials and are constructed utilizing the same coining process as described above.

Any of the markers described herein may be utilized or any of the stent designs illustrated as well as any other stent requiring improved radiopacity.

It is believed that many of the advantages of the present invention can be better understood through a brief description of a delivery apparatus for the stent, as shown in FIGS. 10 and 11. FIGS. 10 and 11 show a self-expanding stent delivery apparatus 10 for a stent made in accordance with the present invention. Apparatus 10 comprises inner and outer coaxial tubes. The inner tube is called the shaft 12 and the outer tube is called the sheath 14. Shaft 12 has proximal and distal ends. The proximal end of the shaft 12 terminates at a luer lock hub 16. Preferably, shaft 12 has a proximal portion 18 which is made from a relatively stiff material such as stainless steel, Nitinol, or any other suitable material, and a distal portion 20 which may be made from a polyethylene, polyimide, Pellethane, Pebax, Vestamid, Cristamid, Grillamid or any other suitable material known to those of ordinary skill in the art. The two portions are joined together by any number of means known to those of ordinary skill in the art. The stainless steel proximal end gives the shaft the necessary rigidity or stiffness it needs to effectively push out the stent, while the polymeric distal portion provides the necessary flexibility to navigate tortuous vessels.

The distal portion 20 of the shaft 12 has a distal tip 22 attached thereto. The distal tip 22 has a proximal end 24 whose diameter is substantially the same as the outer diameter of the sheath 14. The distal tip 22 tapers to a smaller diameter from its proximal end to its distal end, wherein the distal end 26 of the distal tip 22 has a diameter smaller than the inner diameter of the sheath 14. Also attached to the distal portion 20 of shaft 12 is a stop 28 which is proximal to the distal tip 22. Stop 28 may be made from any number of materials known in the art, including stainless steel, and is even more preferably made from a highly radiopaque material such as platinum, gold or tantalum. The diameter of stop 28 is substantially the same as the inner diameter of sheath 14, and would actually make frictional contact with the inner surface of the sheath. Stop 28 helps to push the stent out of the sheath during deployment, and helps keep the stent from migrating proximally into the sheath 14.

A stent bed 30 is defined as being that portion of the shaft between the distal tip 22 and the stop 28. The stent bed 30 and the stent 100 are coaxial so that the distal portion 20 of shaft 12 comprising the stent bed 30 is located within the lumen of the stent 100. However, the stent bed 30 does not make any contact with stent 100 itself. Lastly, shaft 12 has a guidewire lumen 32 extending along its length from its proximal end and exiting through its distal tip 22. This allows the shaft 12 to receive a guidewire much in the same way that an ordinary balloon angioplasty catheter receives a guidewire. Such guidewires are well known in art and help guide catheters and other medical devices through the vasculature of the body.

Sheath 14 is preferably a polymeric catheter and has a proximal end terminating at a sheath hub 40. Sheath 14 also has a distal end which terminates at the proximal end 24 of distal tip 22 of the shaft 12, when the stent is in its fully un-deployed position as shown in the figures. The distal end of sheath 14 includes a radiopaque marker band 34 disposed along its outer surface. As will be explained below, the stent is fully deployed from the delivery apparatus when the marker band 34 is lined up with radiopaque stop 28, thus indicating to the physician that it is now safe to remove the apparatus 10 from the body. Sheath 14 preferably comprises an outer polymeric layer and an inner polymeric layer. Positioned between outer and inner layers is a braided reinforcing layer. Braided reinforcing layer is preferably made from stainless steel. The use of braided reinforcing layers in other types of medical devices can be found in U.S. Pat. No. 3,585,707 issued to Stevens on Jun. 22, 1971, U.S. Pat. No. 5,045,072 issued to Castillo et al. on Sep. 3, 1991, and U.S. Pat. No. 5,254,107 issued to Soltesz on Oct. 19 ,1993.

FIGS. 10 and 11 illustrate the stent 100 as being in its fully un-deployed position. This is the position the stent is in when the apparatus 10 is inserted into the vasculature and its distal end is navigated to a target site. Stent 100 is disposed around stent bed 30 and at the distal end of sheath 14. The distal tip 22 of the shaft 12 is distal to the distal end of the sheath 14, and the proximal end of the shaft 12 is proximal to the proximal end of the sheath 14. The stent 100 is in a compressed state and makes frictional contact with the inner surface 36 of the sheath 14.

When being inserted into a patient, sheath 14 and shaft 12 are locked together at their proximal ends by a Tuohy Borst valve 38. This prevents any sliding movement between the shaft and sheath which could result in a premature deployment or partial deployment of the stent 100. When the stent 100 reaches its target site and is ready for deployment, the Tuohy Borst valve 38 is opened so that that the sheath 14 and shaft 12 are no longer locked together.

The method under which the apparatus 10 deploys the stent 100 is readily apparent. The apparatus 10 is first inserted into the vessel until the radiopaque stent markers 800 (leading 102 and trailing 104 ends, see FIG. 7) are proximal and distal to the target lesion. Once this has occurred the physician would open the Tuohy Borst valve 38. The physician would then grasp hub 16 of shaft 12 so as to hold it in place. Thereafter, the physician would grasp the proximal end of the sheath 14 and slide it proximal, relative to the shaft 12. Stop 28 prevents the stent 100 from sliding back with the sheath 14, so that as the sheath 14 is moved back, the stent 100 is pushed out of the distal end of the sheath 14. As stent 100 is being deployed the radiopaque stent markers 800 move apart once they come out of the distal end of sheath 14. Stent deployment is complete when the marker 34 on the outer sheath 14 passes the stop 28 on the inner shaft 12. The apparatus 10 can now be withdrawn through the stent 100 and removed from the patient.

FIG. 12 illustrates the stent 100 in a partially deployed state. As illustrated, as the stent 100 expands from the delivery device 10, the markers 800 move apart from one another and expand in a flower like manner.

Figure 17:
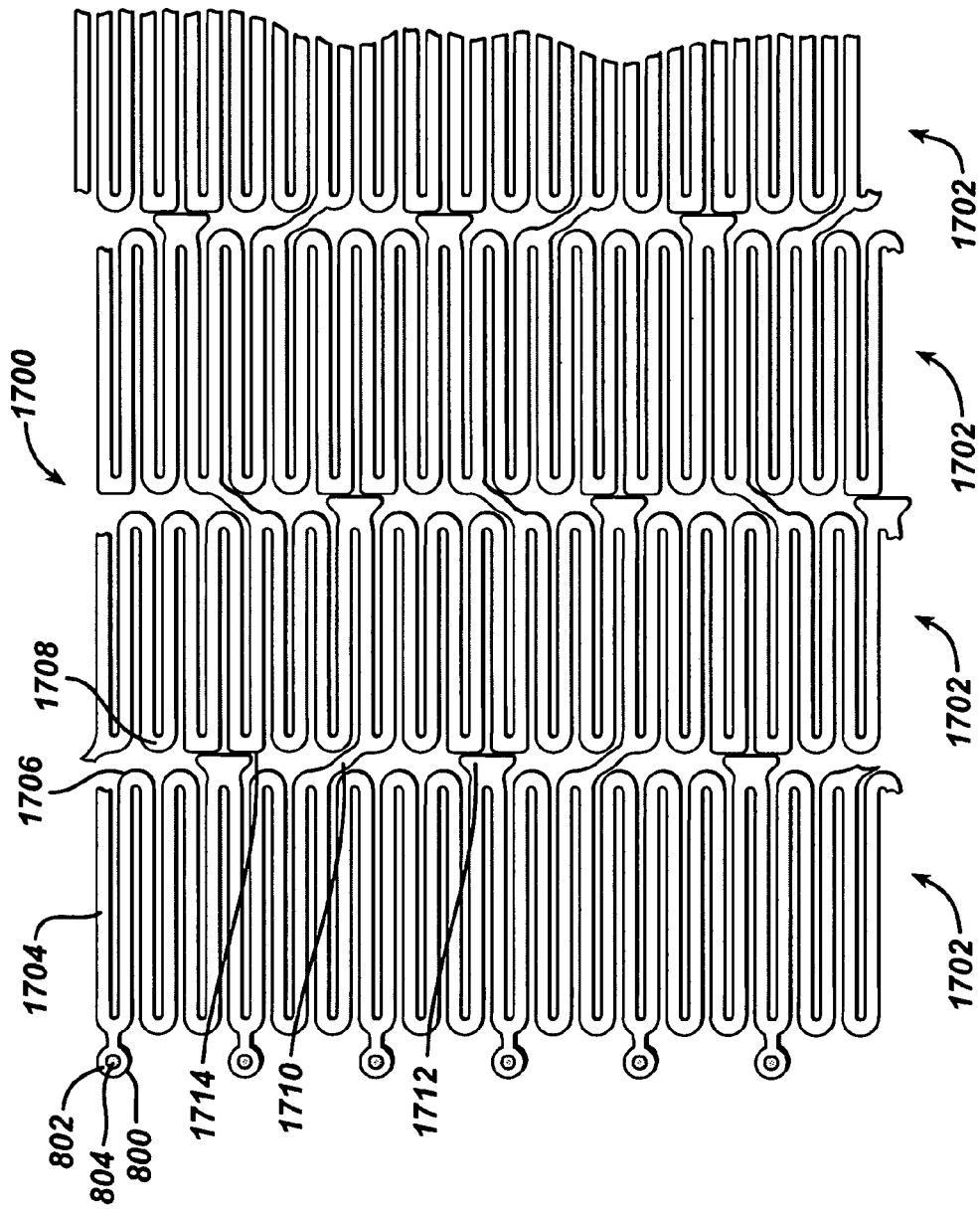
FIG. 17 is a sectional, flat view of an exemplary embodiment of an anvil bridge stent in accordance with the present invention.

FIG. 17 illustrates yet another alternate exemplary embodiment of a self-expanding stent 1700 formed from Nitinol. In this exemplary embodiment, a plurality of anvil bridges are utilized to fill the gap between unbridged loops without serving as a structural connection point between these loops. The split-bridge embodiment described above comprises a pair of structural elements originating from adjacent loops on adjacent hoops. These pairs of structural elements come into contact when the stent is placed in axial compression, thereby providing a means for transmitting axial loading without undesirable deformation of the stent structure or closing of the gaps between hoops and resulting compression of the constrained structure. The anvil bridge embodiment; however, comprises only a single element which originates from one loop and comes into mating or abutting contact with a flattened area of at least one adjacent loop on an adjacent hoop when under axial compression.

As illustrated, the anvil bridge stent 1700 comprises a plurality of adjacent hoops 1702. The hoops 1702 include a plurality of longitudinal struts 1704 and a plurality of loops 1706 connecting adjacent struts 1704, wherein adjacent struts 1704 are connected at opposite ends so as to form a substantially S or Z shape pattern. The loops 1706 are curved, substantially semi-circular with symmetrical sections about their centers 1708. The stent 1700 further comprises a plurality of bridges 1710 which connect adjacent hoops 1702. The bridges 1710 are equivalent to the bridges illustrated in FIGS. 5 and 15 and described above; however, the bridges 1710 may assume a variety of alternate configurations. Also as described above, the bridge orientation is changed from hoop to hoop so as to minimize rotational changes between any two points on a given stent during constraint or deployment. The number of and nature of the design of the struts 1704, loops 1706 and bridges 1710 are important factors when determining the working properties and fatigue life properties of the stent as is discussed in detail above.

The stent 1700 also comprises a plurality of anvil bridges 1712. The anvil bridges 1712 may comprise any suitable configuration and may be positioned in any suitable pattern between bridges 1710. As set forth above, symmetric loading and hence symmetric placement of the bridges, both regular and anvil type, is preferable but not necessary. In the exemplary embodiment illustrated in FIG. 17, the anvil bridges 1712 are centered between bridges 1710 such that a symmetric configuration of bridges 1710 and anvil bridges 1712 results. Unlike the split-bridges described above, the anvil bridge 1712 comprises a one-piece structure which extends from one loop 1706 on one hoop 1702 to a flat surface 1714 formed in two loops 1706 on an adjacent hoop 1702 when the stent is under axial compressive loading. The flat surface 1714 is preferable, but not necessary. The anvil bridge one-piece structure 1712 extends from a single loop 1706 and has an increasing profile until it forms a flat anvil-like surface. The anvil design provides more contact surface area then other designs. This allows the design to be more tolerant of misalignments resulting from variation in constraint diameter and loading deformation. Since the anvil design results in a larger contact surface area, the contact surface area on the adjacent hoop 1702 requires the flat surface 1714 be formed from two longitudinally adjacent loops 1706. Once again, it is important to note that the flat surface 1714 is preferable, but not required. In addition, the contact surface area may comprise one loop, two loops as described, or more than 2 loops. Essentially, the anvil bridge itself is designed to maximize contact surface area and the mating surfaces of the adjacent tips are flattened for the same reason. Furthermore, while the anvil bridge 1712 originates from one loop 1706, the mating contact surfaces 1714 include two loops 1706. All of these factors allow for loading forces to be distributed over a larger area. This allows for more uniform distribution of loading forces throughout the structure, improving stability and decreasing the likelihood of undesirable deformation when the constrained structure is loaded in axial compression.

The geometry of the anvil bridge may take any number of forms which serves the purpose of filling the gaps which may be unoccupied by standard bridges. In addition, the number and arrangement of axial bridges is virtually unlimited.

Figure 18:
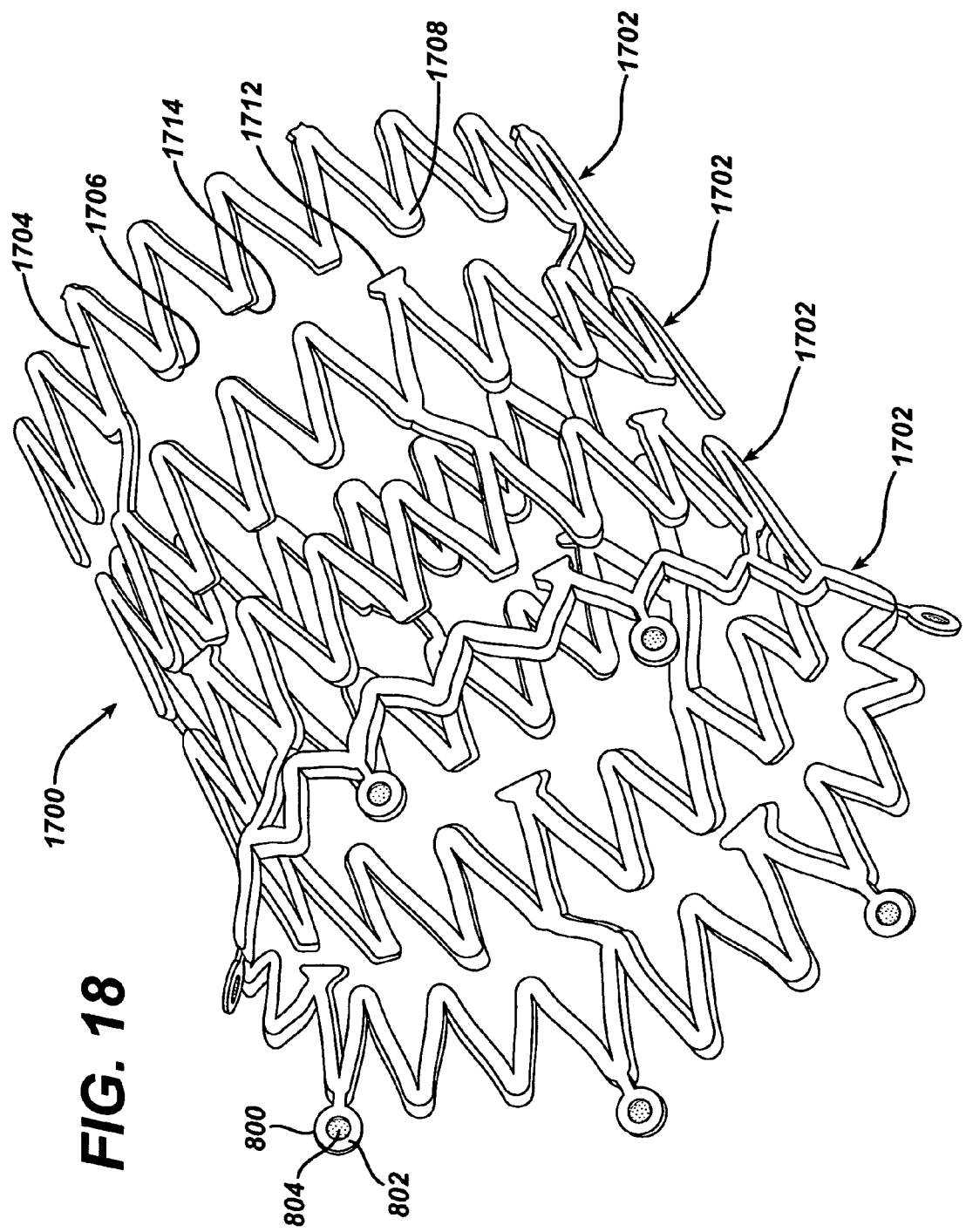
FIG. 18 is a perspective view of the stent illustrated in FIG. 17, but showing the stent in the expanded state.

In this exemplary embodiment, the arrangement of the markers 800, standard bridges 1710 and anvil bridges 1712 was carefully chosen to promote purely axial load transmission through the stent 1700 structure. By its nature, the anvil bridge advantageously allows transmission of compressive loads when constrained because the anvil portion abuts or makes at least partial contact with the contact surface 1714. However, unlike a traditional bridge, it does not transmit tensile or compressive strains when the expanded structure is stretched, compressed or bent. As illustrated in FIG. 18, the anvil bridges 1712 are not aligned once the stent 1700 is expanded. As such, the anvil bridge may provide advantages over a traditional bridge in contourability and fatigue durability.

As stated above, various drugs, agents or compounds may be locally delivered via medical devices such as stents. For example, rapamycin and/or heparin may be delivered by a stent to reduce restenosis, inflammation and coagulation. The additional stent surface area provided by the anvil bridges would be beneficial if an additional amount of the drug, agent, and/or compound is required for a specific dosing, release profile or the like.

Conventional vascular stents generally comprise a series of ring-like radially expandable structural members which are axially connected by bridging elements as described herein. When a stent is subjected to in vivo bending, stretching or compression, its constituent ring-like members distribute themselves accordingly, thereby allowing the stent structure to conform to its vascular surroundings. These loading conditions on the stent structure cause adjacent ring-like structural members (hoops) to change their relative axial position. The ring-like structural members will tend to pull apart from each other or squeeze more closely together depending on local loading conditions. The bridging elements act to constrain adjacent, ring-like members, providing a geometrical structural connection between these members. As such, these bridging elements communicate strain between the adjacent ring-like members.

In an alternate exemplary embodiment, a stent may be constructed from a plurality of individual stent segments which are coupled prior to deployment and which are uncoupled upon deployment. In other words, in this exemplary embodiment, the vascular scaffolding or stent structure comprises individual, independent, self-expanding stent segments, which are designed to interlock when constrained within a stent delivery sheath and uncouple upon deployment as the delivery sheath is retracted.

This alternate exemplary stent design provides a means for reducing or eliminating bridging elements, thereby allowing adjacent ring-like structural members independence from each other. This exemplary design provides for a series of axially independent ring-like members which comprise a composite stent structure. With such a construction, adjacent ring-like members could move relative to one another without inducing strain in the overall structure. As such, the composite stent structure could experience cyclic axial compression or extension, bending, or twisting without experiencing cyclic strain relating to these modes of deformation.

Figure 19:
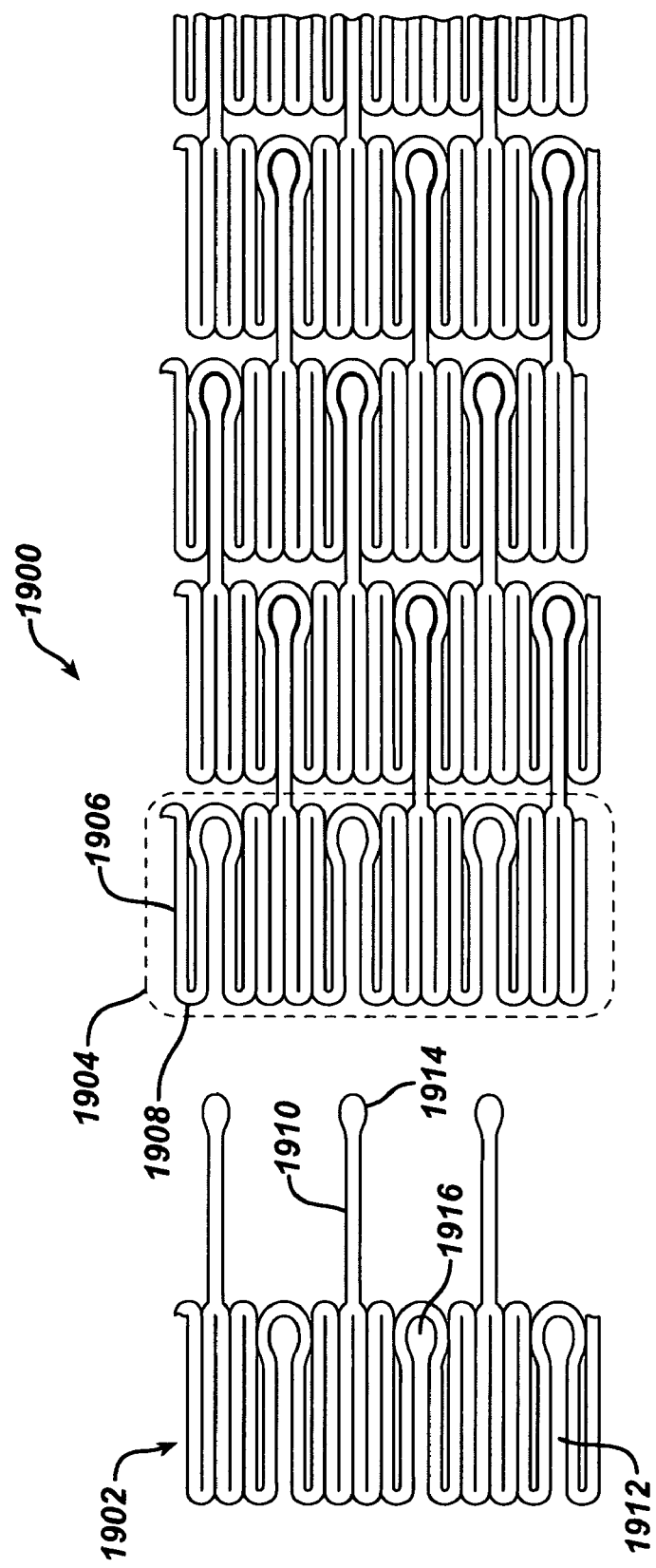
FIG. 19 is a sectional, flat view of an alternate exemplary stent in accordance with the present invention.

FIG. 19 illustrates an exemplary embodiment of a self-expanding, composite stent structure 1900 formed from nitinol. It is important to note, however, that the stent may be constructed from any number of suitable materials. As in the above-described exemplary embodiments, each stent segment 1902 of the stent structure comprises a hoop 1904 formed from a plurality of longitudinal struts 1906 and a plurality of loops 1908 connecting adjacent longitudinal struts 1906, wherein adjacent longitudinal struts 1906 are connected at opposite ends so as to form a substantially "S" or "Z" shape patterns. As illustrated, the individual stent segments 1902 are constructed as simple "S" or "Z" shaped structures; however, in alternate exemplary embodiments, the individual segments 1902 may comprise any number of design variations, including short segments of conventional stents or similar hybrid designs.

Each individual stent segment 1902 comprises a number of bridging elements 1910 and a number of receptacles 1912. The bridging elements 1910 are designed to mate with and engage the receptacles 1912 on adjacent stent segments 1902. The bridging elements 1910 protrude from a predetermined number of loops 1908 on each stent segment 1902. The number of bridging elements 1910 depends on a number of factors including the radial size or diameter of the stent 1900. The receptacles 1912 are formed by creating additional space between adjacent longitudinal struts 1906 and expanding certain loops 1908. Each bridging element 1910 includes a protrusion 1914 that fits within a cavity 1916 of each receptacle 1912 when the individual stent segments 1902 are properly nested together and restrained. The delivery system for this exemplary stent is designed such that the bridging elements 1910 of the most proximal stent segment 1902 mate with a collar having cavities similar to the cavities 1916 in the receptacles 1912 as described in more detail subsequently. In this exemplary embodiment, the protrusions 1914 and the corresponding cavities 1916 have a substantially oval shape. However, in alternate exemplary embodiments, any shape may be utilized.

It is important to note that many stent design variations may be utilized. In the design illustrated in FIG. 19, the stent segments 1902 are not nested. In other words, the longitudinal struts 1906 of one stent segment 1902 does not fit within the longitudinal struts 1906 of an adjacent stent segment 1902. However, by shortening the bridging element 1910, or some other suitable arrangement the stent segments 1902 may be nested. Basically, shortening the bridging elements 1910 allows for nesting of the stent segments 1902, and nested segments allow for better coverage. However, longer bridging elements 1910 allow for better deployment stability.

Figure 20:
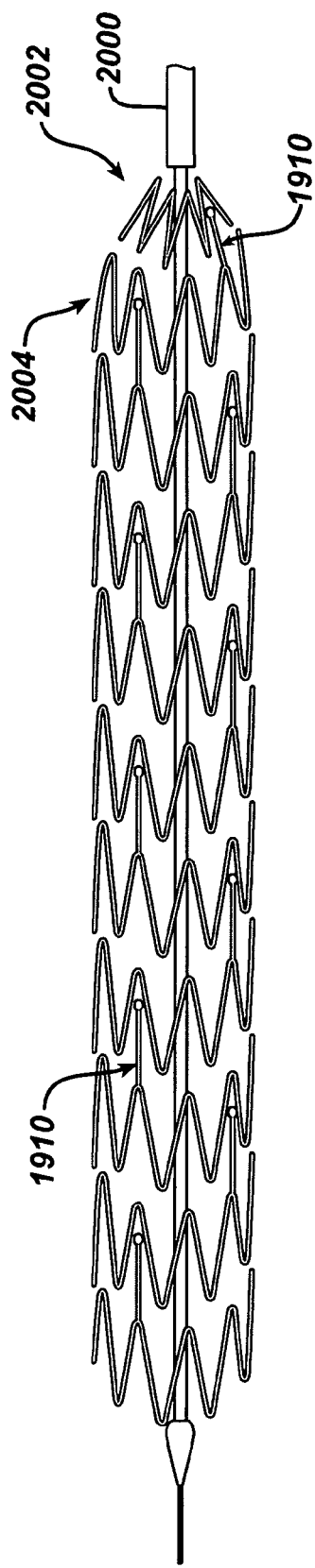
FIG. 20 is a perspective view of the stent shown in FIG. 19, but showing it in its expanded state.

FIG. 20 illustrates the deployment of the individual stent segments 1902 which uncouple as the sheath 2000 is retracted. As the sheath 2000 is retracted, the individual stent segments 1902 begin to exit the delivery system and expand to their full diameter. As a segment 1902 exits the sheath 2000, it remains coupled to its proximally adjacent segment 1902, as illustrated at 2002. As the sheath 2000 is further retracted and the stent segment 1902 achieves opposition to the vessel wall, as illustrated at 2004, the next stent segment 1902 begins to deploy from the sheath 2000, thus releasing the bridging element 1910. Once fully deployed, the individual stent segments 1902 are fully independent from adjacent segments. The bridging elements 1910 remain, but are no longer coupled.

A significant advantage of this exemplary stent is the ability to deploy individual stent segments in a controlled fashion. The interlocking coupling may be designed such that it does not disengage a deployed segment from the delivery system until it is firmly opposed to the vessel wall. Without such a mechanism, short individual segments could potentially propel themselves out of the delivery system in an uncontrolled fashion as they expand to their full diameter.

Figure 21:
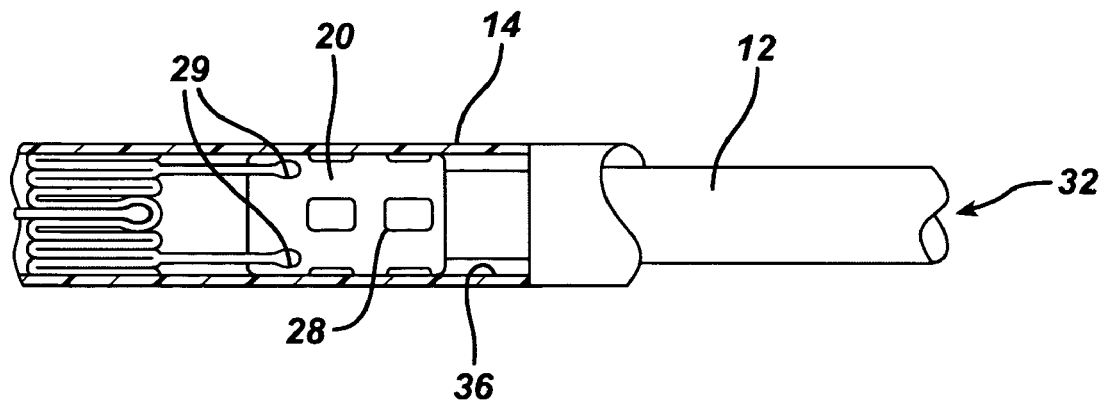
FIG. 21 is a diagrammatic representation of a delivery device in accordance with the present invention.

FIG. 21 illustrates and exemplary delivery device in accordance with the present invention. The exemplary delivery device is substantially identical to the delivery device described herein and illustrated in FIGS. 10 and 11. In this exemplary embodiment, the shaft 12 may comprise a collar or a modified stop 28. As illustrated the modified stop/collar 28 comprises mating openings 29 that correspond in shape to the cavities 1916 of the stent segments 1902 (FIG. 19). The number of mating openings 29 depends on the number of bridging elements 1910 (FIG. 19). In addition, the delivery device may be utilized to deploy a given number of stent segments thereby allowing the physician to treat various size lesions and/or multiple lesions.

In yet another alternate exemplary embodiment, the radiopaque markers disclosed herein may be incorporated into the design of the individual stent segments. For example, the markers illustrated in FIGS. 7, 8 and 9 may be incorporated into the bridging elements 1910. Rather than a simple protrusion 1914 at the end of the bridging element 1910, a marker housing and marker insert may be utilized. Accordingly, the markers would serve a dual purpose. Alternately, the end segments may comprise the markers as described above.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed is:

1. An intraluminal medical device comprising multiple, independent, self-expanding stent segments, each stent segment including a plurality of longitudinal struts, a plurality of loops connecting adjacent struts, at least one bridging element comprising an elongate member extending from one of the plurality of loops and having a free end with a mating protrusion, the elongate member being longer than the plurality of longitudinal struts, and at least one receptacle, the at least one receptacle comprising an additional space between adjacent longitudinal struts and an expanded loop, defining a cavity for the elongate member and the mating protrusion wherein the at least one bridging element of one or more of the stent segments is configured to be releasably engaged with the at least one receptacle on an adjacent stent segment and wherein the at least one bridging element on one stent segment is offset radially with respect to the at least one bridging element on an adjacent stent segment such that each bridging element in one stent segment does not line up with any bridging element on an adjacent stent segment.

2. The intraluminal medical device according to claim 1, wherein the cavity and the mating protrusion have a substantially oval shape.

3. The intraluminal medical device according to claim 2, wherein the self-expanding stent segments comprise a superelastic alloy.

4. The intraluminal medical device according to claim 3, wherein the superelastic alloy comprises from about fifty percent to about sixty percent Nickel and the remainder titanium.

5. The intraluminal medical device according to claim 1, wherein the plurality of struts and the plurality of loops form a substantially S-shaped configuration.

6. The intraluminal medical device according to claim 1, further comprising one or more radiopaque markers.

7. The intraluminal medical device according to claim 6, wherein the one or more markers are incorporated into the mating protrusion.

* * * * *